United States Patent
Kai et al.

(10) Patent No.: US 9,156,843 B2
(45) Date of Patent: *Oct. 13, 2015

(54) ORGANIC ELECTROLUMINESCENT DEVICE COMPRISING AN ORGANIC LAYER CONTAINING AN INDOLOCARBAZOLE COMPOUND

(75) Inventors: Takahiro Kai, Kitaktyushu (JP); Masaki Komori, Kitakyushu (JP); Toshihiro Yamamoto, Kitakyushu (JP); Megumi Matsumoto, Kitakyushu (JP)

(73) Assignee: NIPPON STEEL & SUMIKIN CHEMICAL CO., LTD., Tokyo (JP)

( * ) Notice: Subject to any disclaimer, the term of this patent is extended or adjusted under 35 U.S.C. 154(b) by 39 days.

This patent is subject to a terminal disclaimer.

(21) Appl. No.: 13/577,238

(22) PCT Filed: Jan. 27, 2011

(86) PCT No.: PCT/JP2011/051639
§ 371 (c)(1),
(2), (4) Date: Aug. 4, 2012

(87) PCT Pub. No.: WO2011/099374
PCT Pub. Date: Aug. 18, 2011

(65) Prior Publication Data
US 2012/0305903 A1    Dec. 6, 2012

(30) Foreign Application Priority Data
Feb. 12, 2010    (JP) .................. 2010-028567

(51) Int. Cl.
H01L 51/54    (2006.01)
C09K 11/06    (2006.01)
C07D 487/04    (2006.01)
H01L 51/00    (2006.01)
H05B 33/14    (2006.01)
C07D 487/14    (2006.01)
C07D 471/14    (2006.01)
(Continued)

(52) U.S. Cl.
CPC ............ *C07D 487/04* (2013.01); *C07D 471/14* (2013.01); *C07D 487/14* (2013.01); *C07D 519/00* (2013.01); *C09K 11/06* (2013.01); *H01L 51/0072* (2013.01); *H05B 33/14* (2013.01); *C09K 2211/1044* (2013.01); *H01L 51/0067* (2013.01); *H01L 51/0074* (2013.01); *H01L 51/0085* (2013.01); *H01L 51/5012* (2013.01); *H01L 51/5016* (2013.01); *H01L 51/5048* (2013.01); *H01L 51/5096* (2013.01)

(58) Field of Classification Search
None
See application file for complete search history.

(56) References Cited

U.S. PATENT DOCUMENTS 5,843,607 A    12/1998    Hu et al.
5,942,340 A    8/1999    Hu et al.
5,952,115 A    9/1999    Hu et al.
(Continued)

FOREIGN PATENT DOCUMENTS

JP    2008-513441 A    5/2008
JP    2009-085657    3/2009
(Continued)

OTHER PUBLICATIONS

Sigma-Aldrich website page for Tris[2-(4,6-difluorophenyl)pyridinato-C2,N]iridium(III) 96%. Date of publication: Feb. 6, 2014.*

(Continued)

*Primary Examiner* — Andrew K Bohaty
(74) *Attorney, Agent, or Firm* — Cheng Law Group, PLLC

(57) ABSTRACT

Disclosed is an organic electroluminescent device (organic EL device) that is improved in luminous efficiency, sufficiently secures driving stability, and has a simple configuration. This organic EL device is constituted of an anode, organic layers comprising a phosphorescent light-emitting layer, and a cathode piled one upon another on a substrate and at least one organic layer selected from a light-emitting layer, an electron-transporting layer, and a hole-blocking layer contains an indolocarbazole compound represented by general formula (1). In the case where the indolocarbazole compound is incorporated in the light-emitting layer containing a phosphorescent dopant and a host material, it is incorporated as the host material. Some of such indolocarbazole compounds are represented by the following formula (2): wherein each of $A_1$ and $A_2$ is an aromatic hydrocarbon group; each of $B_1$ and $B_2$ is an aromatic heterocyclic group; each of $R_1$ to $R_3$ is a hydrogen atom, an alkyl group, a cycloalkyl group, an aromatic hydrocarbon group, or an aromatic heterocyclic group; m is an integer of 1 to 3; and n is an integer of 0 to 3.

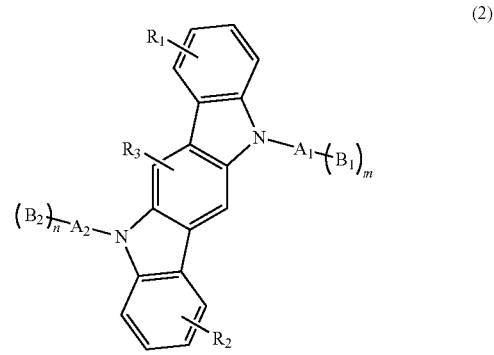

18 Claims, 2 Drawing Sheets

(51) Int. Cl.
*C07D 519/00* (2006.01)
*H01L 51/50* (2006.01)

(56) References Cited

U.S. PATENT DOCUMENTS

| | | |
|---|---|---|
| 7,452,615 B2 | 11/2008 | Kim et al. |
| 2002/0034655 A1 | 3/2002 | Watanabe et al. |
| 2009/0295276 A1 | 12/2009 | Asari et al. |
| 2009/0302742 A1* | 12/2009 | Komori et al. ............... 313/504 |
| 2009/0302743 A1 | 12/2009 | Kato et al. |
| 2009/0309488 A1 | 12/2009 | Kato et al. |
| 2010/0012931 A1 | 1/2010 | Kato et al. |
| 2010/0187977 A1 | 7/2010 | Kai et al. |
| 2010/0213452 A1* | 8/2010 | Sisk et al. ....................... 257/40 |
| 2011/0062429 A1 | 3/2011 | Kai et al. |
| 2011/0062862 A1 | 3/2011 | Yamamoto et al. |
| 2012/0007070 A1 | 1/2012 | Kai et al. |

FOREIGN PATENT DOCUMENTS

| | | | |
|---|---|---|---|
| KR | 2010131939 A | * | 12/2010 |
| WO | WO-01/41512 A1 | | 6/2001 |
| WO | WO-2007/063754 A1 | | 6/2007 |
| WO | WO-2009/136595 A1 | | 11/2009 |
| WO | WO-2009/136596 A1 | | 11/2009 |
| WO | WO-2010/113761 A1 | | 10/2010 |

OTHER PUBLICATIONS

Gu et al. Synlett 2006, 10, 1535-1538. Date of online publication: Dec. 6, 2006.*

Wu et al. J. Am. Chem. Soc. 2005, 127, 614-618. Date of online publication: Dec. 9, 2004.*

Machine translation of KR2010-131939. Date of publication: Dec. 16, 2010.*

Notification of Reasons for Refusal for the Application No. 2011-553796 from Japan Patent Office mailed Dec. 11, 2012.

International Search Report for the Application No. PCT/JP2011/051839 mailed Apr. 12, 2011.

International Preliminary Report on Patentability for the Application No. PCT/JP2011/051639 mailed Oct. 11, 2012.

* cited by examiner

ORGANIC ELECTROLUMINESCENT DEVICE COMPRISING AN ORGANIC LAYER CONTAINING AN INDOLOCARBAZOLE COMPOUND

JOINT RESEARCH AGREEMENT

The present invention was made by Nippon Steel & Sumikin Chemical Co., Ltd. based on a Joint Research Agreement between Nippon Steel & Sumikin Chemical Co., Ltd. and Universal Display Corporation. The Joint Research Agreement was executed on Oct. 1, 2008 and was in effect on or before the date the claimed invention was made. The Joint Research Agreement relates to the field of organic electroluminescent devices.

TECHNICAL FIELD

This invention relates to an organic electroluminescent device containing an indolocarbazole compound and, more particularly, to a thin film type device that emits light upon application of an electric field to a light-emitting layer composed of an organic compound.

BACKGROUND TECHNOLOGY

An organic electroluminescent device (hereinafter referred to as organic EL device) in the simplest structure is generally constituted of a light-emitting layer and a pair of counter electrodes holding the light-emitting layer between them. The organic EL device functions by utilizing the following phenomenon; upon application of an electric field between the electrodes, electrons are injected from the cathode and holes are injected from the anode and they recombine in the light-emitting layer with emission of light.

In recent years, studies have been started to develop organic EL devices in which organic thin films are used. In particular, in order to enhance the luminous efficiency, the kind of electrodes has been optimized for the purpose of improving the efficiency of injecting carriers from the electrodes and a device has been developed in which a hole-transporting layer composed of an aromatic diamine and a light-emitting layer composed of 8-hydroxyquinoline aluminum complex (hereinafter referred to as Alq3) are disposed in thin film between the electrodes. This device has brought about a marked improvement in the luminous efficiency over the conventional devices utilizing single crystals of anthracene and the like and thereafter the developmental works of organic EL devices have been directed toward practical applications to high-performance flat panels featuring self-luminescence and high-speed response.

Further, in an effort to enhance the luminous efficiency of the device, the use of phosphorescence in place of fluorescence is investigated. The aforementioned device comprising a hole-transporting layer composed of an aromatic diamine and a light-emitting layer composed of Alq3 and many others have utilized fluorescence. However, the utilization of phosphorescence, that is, emission of light from the triplet excited state, is expected to enhance the luminous efficiency three to four times that of the conventional devices utilizing fluorescence (emission of light from the singlet excited state). To achieve this objective, the use of coumarin derivatives and benzophenone derivatives in the light-emitting layer was investigated, but these derivatives merely produced luminance at an extremely low level. Europium complexes were also investigated in trials to utilize the excited triplet state, but they too failed to emit light at high efficiency. In recent years, as stated in patent document 1, a large number of researches are conducted on phosphorescent dopant materials, with a focus on the use of organic metal complexes such as iridium complexes, for the purpose of enhancing the luminous efficiency and extending the life.

PRIOR ART TECHNICAL DOCUMENTS

Patent Documents

Patent document 1: JP 2003-515897 A
Patent document 2: JP 2001-313178 A
Patent document 3: JP Hei 11-162650 A
Patent document 4: JP Hei 11-176578 A
Patent document 5: WO 2008-056746

In order to obtain high luminous efficiency, a host material to be used together with the aforementioned dopant material becomes important. Of the host materials proposed thus far, a typical example is 4,4'-bis(9-carbazolyl)biphenyl (hereinafter referred to as CBP) presented in patent document 2. Since CBP is characterized by having a good hole transfer property but a poor electron transfer property, the use of CBP as a host material for tris(2-phenylpyridine)iridium complex (hereinafter referred to as Ir(ppy)$_3$), a typical phosphorescent green light-emitting material, disturbs the balanced injection of charges and causes excessive holes to flow out to the side of the electron-transporting layer. The results is a reduction in the luminous efficiency of Ir(ppy)$_3$.

In order for an organic EL device to display high luminous efficiency, a host material that has a high triplet excitation energy and is well balanced in the injection and transportation characteristics of electric charges (holes and electrons) is required. Furthermore, compounds that are electrochemically stable, highly resistant to heat, and excellently stable in the amorphous state are desired and further improvements are demanded.

Patent document 3 discloses the indolocarbazole compound illustrated below as a hole-transporting material.

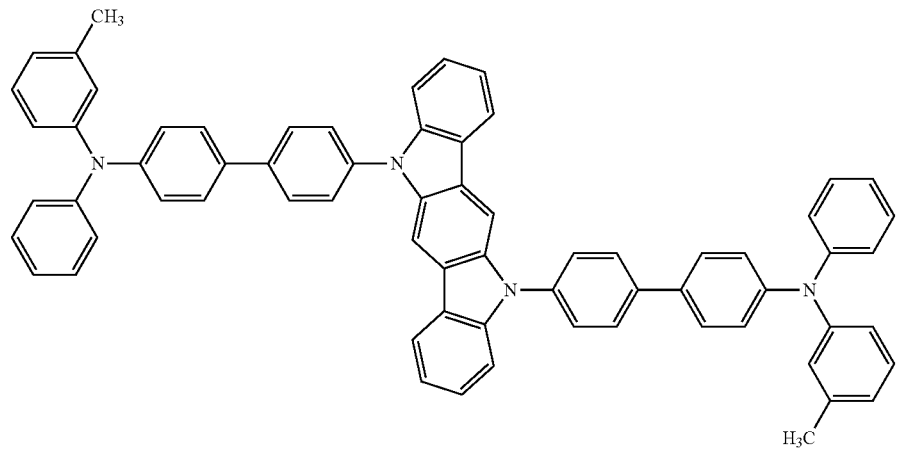 [SMILES: Cc1cccc(N(c2ccccc2)c2ccc(-c3ccc(-n4c5ccccc5c5cc6c(cc54)c4ccccc4n6-c4ccc(-c5ccc(N(c6ccccc6)c6cccc(C)c6)cc5)cc4)cc3)cc2)c1]

Further, patent document 4 discloses the indolocarbazole compound illustrated below as a hole-transporting material.

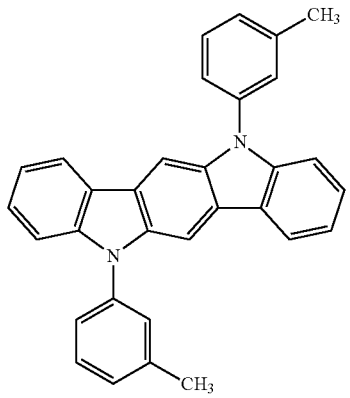 [SMILES: Cc1cccc(-n2c3ccccc3c3cc4c(cc32)c2ccccc2n4-c2cccc(C)c2)c1]

However, these patent documents recommend the use of compounds having an indolocarbazole skeleton as hole-transporting materials and the examples in the documents demonstrate such use only in the case of fluorescent light-emitting devices. Therefore, it cannot be said that the use as a material for a phosphorescent light-emitting device is disclosed.

Still further, patent document 5 discloses the indolocarbazole compound illustrated below.

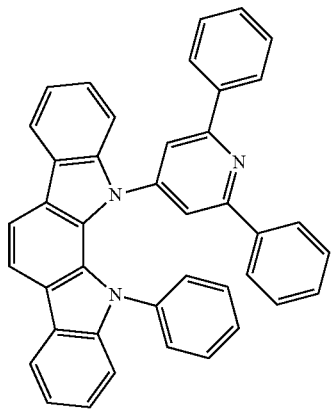 [SMILES: c1ccc(-c2cc(-n3c4ccccc4c4ccc5c6ccccc6n(-c6ccccc6)c5c43)cc(-c3ccccc3)n2)cc1]

However, a hydrogen atom on one of the nitrogen atoms in the indolocarbazole skeleton of the aforementioned compound is replaced directly by an aromatic heterocyclic ring and it cannot be said that the document discloses the use of an aromatic hydrocarbon group as a linking group.

DISCLOSURE OF THE INVENTION

In applications of organic EL devices to display devices such as flat panel displays, it is necessary to enhance the luminous efficiency of the device and, at the same time, to sufficiently secure the driving stability of the device. Under the aforementioned circumstances, an object of this invention is to provide an organic EL device exhibiting such luminous efficiency and driving stability as to be practically useful and to provide a compound suitable therefor.

The inventors of this invention have conducted intensive studies, found that the use of an indolocarbazole compound in which the indolocarbazole skeleton is linked to an aromatic heterocyclic group via an aromatic hydrocarbon group displays excellent characteristics when used in an organic EL device, and completed this invention.

This invention relates to an organic electroluminescent device comprising an anode, organic layers containing a phosphorescent light-emitting layer, and a cathode piled one upon another on a substrate wherein at least one organic layer selected from a light-emitting layer, an electron-transporting layer, and a hole-blocking layer contains an indolocarbazole compound represented by general formula (1).

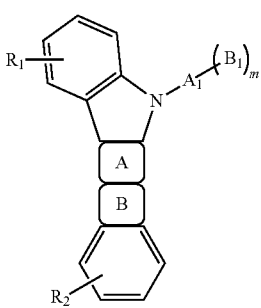

(1)

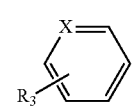

(1a)

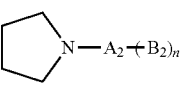

(1b)

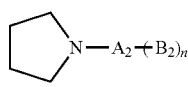

In general formulas (1), ring A is an aromatic ring or a heterocyclic ring represented by formula (1a) and fused to the adjacent rings at arbitrary positions and ring B is a heterocyclic ring represented by formula (1b) and fused to the adjacent rings at arbitrary positions. In general formula (1) and formulas (1a) and (1b), each of $A_1$ and $A_2$ is independently an aromatic hydrocarbon group of 6 to 50 carbon atoms; each of $B_1$ and $B_2$ is independently an aromatic heterocyclic group of 3 to 50 carbon atoms; X is a methine group or a nitrogen atom; each of $R_1$ and $R_2$ is independently a hydrogen atom, an aliphatic hydrocarbon group of 1 to 10 carbon atoms, an aromatic hydrocarbon group of 6 to 12 carbon atoms, or an aromatic heterocyclic group of 3 to 11 carbon atoms; $R_3$ is a hydrogen atom, an aliphatic hydrocarbon group of 1 to 10 carbon atoms, an aromatic hydrocarbon group of 6 to 12 carbon atoms, or an aromatic heterocyclic group of 3 to 11 carbon atoms and it may be fused to the ring containing X to form a fused ring; m is an integer of 1 to 3; n is an integer of 0 to 3; when m or n is 2 or more, a plurality of $B_1$s or $B_2$s may be identical with or different from one another.

Of the indolocarbazole compounds represented by general formula (1), those represented by the following general formulas (2) to (5) are preferred.

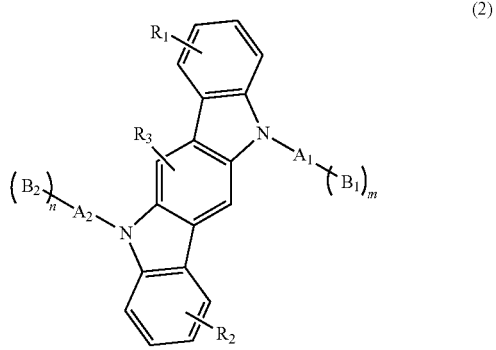

(2)

(3)

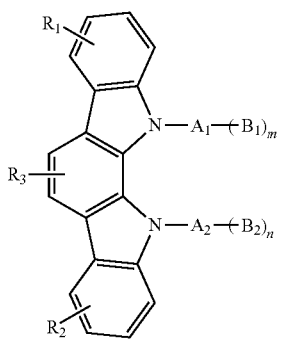

(4)

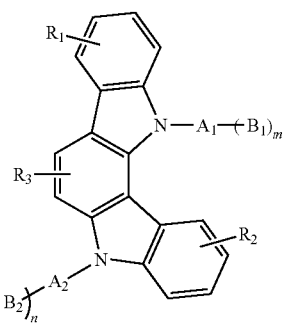

(5)

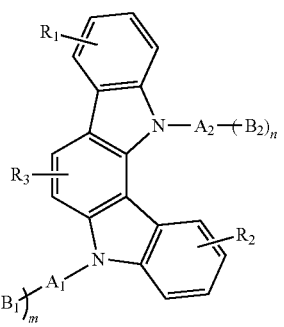

(7)

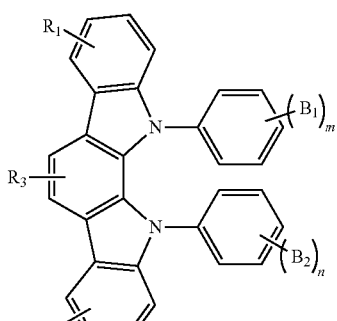

(8)

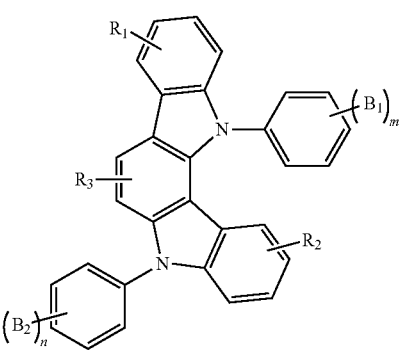

(9)

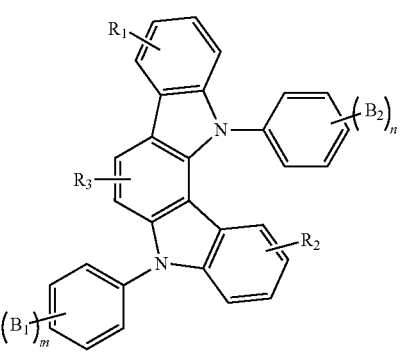

In general formulas (2) to (5), $A_1$, $A_2$, $B_1$, $B_2$, $R_1$ to $R_3$, m, and n respectively have the same meaning as those in general formula (1).

Of the indolocarbazole compounds represented by any of general formulas (2) to (5), those represented by any of the following general formulas (6) to (9) are more preferred.

(6)

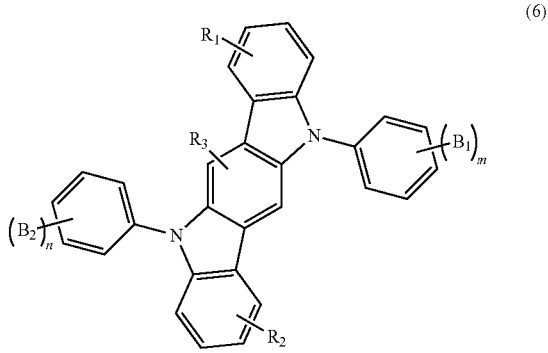

In general formulas (6) to (9), $B_1$, $B_2$, $R_1$ to $R_3$, m, and n respectively have the same meaning as those in general formula (1).

It is preferable that an organic layer containing the aforementioned indolocarbazole compound is a light-emitting layer containing a phosphorescent dopant.

It is particularly preferable that an organic layer containing an indolocarbazole compound is a light-emitting layer containing a phosphorescent dopant having a peak emission wavelength of 440 to 510 nm and an indolocarbazole compound represented by either of general formulas (4) and (5).

It is conceivable that an indolocarbazole compound represented by general formula (1) displays good injection and transportation characteristics of holes and electrons and high durability as a result of the indolocarbazole skeleton being linked to at least one aromatic heterocyclic ring via an aromatic hydrocarbon group. An organic EL device using the said indolocarbazole compound functions at low driving voltage and, particularly in the case where the said indolocarbazole compound is incorporated in the light-emitting layer, the balance of electric charges improves with the resultant improvement in the probability of their recombination. Moreover, the compound in question is characterized by having high energy in the lowest triplet excited state and an ability to suppress effectively transfer of the triplet excitation energy from the dopant to the host molecule and these properties conceivably provide excellent light-emitting characteristics. In addition, the compound has a good property in the amorphous state, high heat resistance, and electrochemical stability and properties such as these likely contribute to realization of organic EL devices of long driving life and high durability.

PREFERRED EMBODIMENTS OF THE INVENTION

Figure 1:
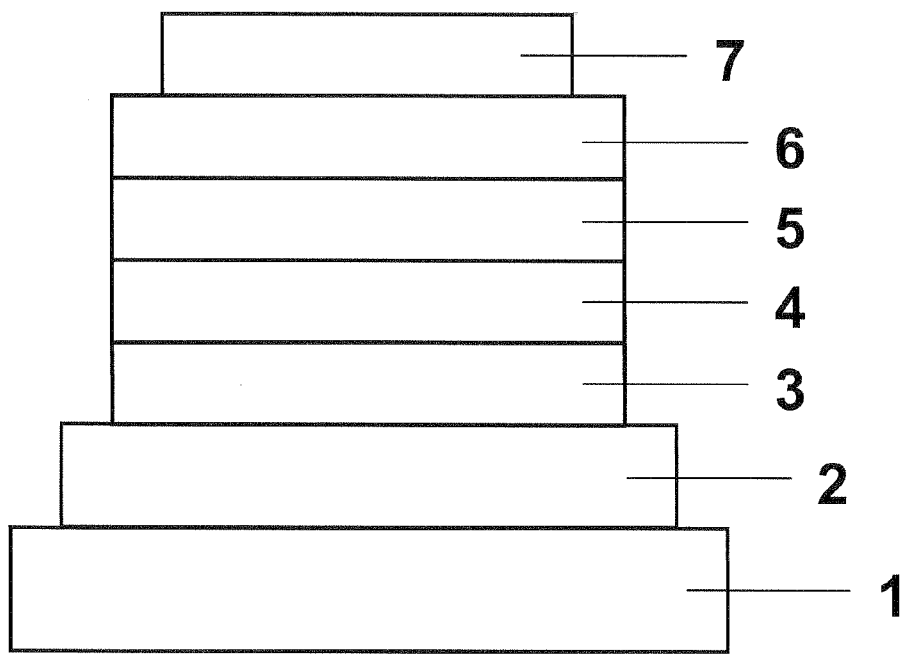
FIG. 1 shows an example of the structure of an organic EL device.

An organic electroluminescent device according to this invention contains an indolocarbazole compound represented by the aforementioned general formula (1). This indolocarbazole compound has a structure wherein the substituents on the two nitrogen atoms are aromatic hydrocarbon groups at least one of which is an aromatic heterocyclic group and it is conceivable that this specific structure produces an excellent effect.

In general formula (1), ring A is an aromatic ring or a heterocyclic ring represented by formula (1a) and fused to the adjacent rings at arbitrary positions and ring B is a heterocyclic ring represented by formula (1b) and fused to the adjacent rings at arbitrary positions.

In general formula (1), each of $A_1$ and $A_2$ is independently an aromatic hydrocarbon group of 6 to 50 carbon atoms, preferably an aromatic hydrocarbon group of 6 to 30 carbon atoms, more preferably an aromatic hydrocarbon group of 6 to 18 carbon atoms; $A_1$ is an (m+1)-valent aromatic hydrocarbon group and $A_2$ is an (n+1)-valent aromatic hydrocarbon group. Specific examples of $A_1$ or $A_2$ include (m+1)-valent or (n+1)-valent groups formed by removing hydrogen atoms from aromatic hydrocarbons such as benzene, naphthalene, fluorene, anthracene, phenanthrene, fluoranthene, pyrene, and chrysene or from aromatic compounds in which a plurality of these aromatic hydrocarbons are linked together. In the case where a plurality of aromatic hydrocarbons are linked together, the total number of carbon atoms is 10 to 50. Preferable examples include groups derived from benzene, naphthalene, anthracene, and phenanthrene and more preferable examples include groups derived from benzene. In the case where the aforementioned aromatic hydrocarbons are linked together, they may be identical with or different from one another and the number of linked aromatic hydrocarbons is preferably 2 to 5, more preferably 2 or 3. Specific examples of groups formed by removing hydrogen atoms from the aforementioned linked aromatic hydrocarbons include groups derived from biphenyl, terphenyl, phenylnaphthalene, diphenylnaphthalene, phenylanthracene, diphenylanthracene, and diphenylfluorene. The position of linkage between $A_1$ and indolocarbazole or between $A_1$ and $B_1$ is not limited and linkage may involve a ring at the end or in the middle. The aforementioned aromatic hydrocarbon groups may have a substituent. In case they have a substituent, preferable examples thereof include an alkyl group of 1 to 4 carbon atoms, an alkoxyl group of 1 to 2 carbon atoms, and an acetyl group.

When the groups derived from aromatic compounds in which a plurality of aromatic rings are linked together are divalent, such divalent groups are represented, for example, by the following formulas (11) to (13).

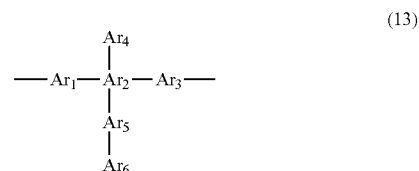

(In formulas (11) to (13), each of $Ar_1$ to $Ar_6$ is an unsubstituted monocyclic or fused aromatic ring.)

In the case where $A_1$ and $A_2$, $B_1$ and $B_2$, or $R_1$ to $R_3$ are respectively aromatic hydrocarbon groups, aromatic heterocyclic groups, or aliphatic hydrocarbon groups and have substituents, the number of substituents is 1 to 10, preferably 1 to 6, more preferably 1 to 4. In case there are two or more substituents, they may be identical with or different from one another. The number of carbon atoms in the substituents is included in computing the number of carbon atoms in the aforementioned aromatic hydrocarbon groups, aromatic heterocyclic groups, or aliphatic hydrocarbon groups.

In general formula (1), each of $B_1$ and $B_2$ is independently a monovalent aromatic heterocyclic group of 3 to 50 carbon atoms, preferably an aromatic heterocyclic group of 3 to 30 carbon atoms, more preferably an aromatic heterocyclic group of 3 to 17 carbon atoms. However, neither $B_1$ nor $B_2$ can be an indolocarbazolyl group. In the case where a plurality of aromatic heterocyclic rings are linked together, the total number of carbon atoms is 6 to 50. Specific examples of $B_1$ and $B_2$ include monovalent groups derived from pyrrole, pyridine, pyrimidine, triazine, indole, quinoline, isoquinoline, quinoxaline, naphthyridine, carbazole, acridine, furan, benzofuran, dibenzofuran, thiopene, benzothiophene, and dibenzothiophene or from aromatic compounds in which a plurality of these compounds are linked together. Preferable examples include monovalent groups derived from pyridine, pyrimidine, triazine, carbazole, dibenzofuran, and dibenzothiophene. In the case where a plurality of the aforementioned aromatic compounds are linked together, they may be identical with or different from one another. In this case, the number of linked aromatic compounds is preferably 2 to 5, more preferably 2 or 3. Specific examples of groups formed by removing a hydrogen atom respectively from the aforementioned linked aromatic compounds include monovalent groups derived from bipyridine, bipyrimidine, bitriazine, pyridylpyrimidine, pyridylcarbazole, and pyrimidylcarbazole. The aforementioned aromatic heterocyclic rings may have a substituent. In case they have a substituent, preferable examples thereof include an alkyl group of 1 to 4 carbon atoms, an alkoxyl group of 1 to 2 carbon atoms, an acetyl group, and an aromatic hydrocarbon group of 6 to 12 carbon atoms. Preferable examples include a phenyl group and a naphthyl group.

In general formula (1), m is an integer of 1 to 3, preferably 1 or 2. When m is 2 or more, Bis may be identical with or different from one another. The symbol n is an integer of 0 to 3, preferably an integer of 0 to 2. When n is 2 or more, $B_2$s may be identical with or different from one another. It is preferable here that m+n is 1 to 3.

In general formula (1), each of $R_1$ and $R_2$ is independently a hydrogen atom, an aliphatic hydrocarbon group of 1 to 10 carbon atoms, an aromatic hydrocarbon group of 6 to 12 carbon atoms, or an aromatic heterocyclic group of 3 to 11 carbon atoms; preferably a hydrogen atom, an alkyl group of 1 to 4 carbon atoms, a cycloalkyl group of 3 to 6 carbon atoms, a phenyl group, a naphthyl group, a pyridyl group, a pyrimidyl group, a triazyl group, or a carbazolyl group; more preferably a hydrogen atom, a phenyl group, or a carbazolyl group.

In general formula (1), $R_3$ is a hydrogen atom, an aliphatic hydrocarbon group of 1 to 10 carbon atoms, an aromatic hydrocarbon group of 6 to 12 carbon atoms, an aromatic heterocyclic group of 3 to 11 carbon atoms, or a group to be fused to the ring containing X. In the case where $R_3$ is a group to be fused to the six-membered ring containing X in formula (1a) and it is in the form of a ring, the ring may be a fused ring. In case the ring is a fused ring, it is preferably an indole ring. In this case, the fusion of the indole ring leads to formation of diindolocarbazole. The indole ring here may have a substituent.

Of the indolocarbazole compounds represented by general formula (1), those represented by the aforementioned general formulas (2) to (5) are preferred and those represented by the aforementioned general formulas (6) to (9) are more preferred.

In general formulas (1) to (9), it is to be understood that the same symbols and formulas have the same meaning unless otherwise indicated.

The indolocarbazole compounds represented by general formulas (1) to (9) can be synthesized by selecting raw materials according to the structure of the target compound and using a known technique.

For example, the indolocarbazole skeleton represented by general formula (2) or (6) can be synthesized by the reaction formula shown below with reference to a synthetic example described in Archive der Pharmazie (Weiheim, Germany), 1987, 320 (3), pp 280-282.

Further, the indolocarbazole skeleton of the indolocarbazole compound represented by general formula (3) or (7) can be synthesized by the reaction formula shown below with reference to a synthetic example described in Synlett., 2005, No. 1, pp 42-48.

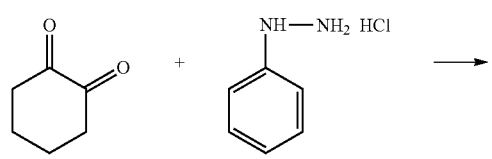

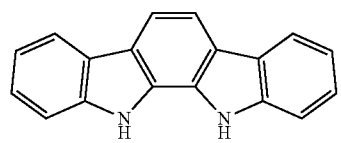

Still further, the indolocarbazole skeleton of the indolocarbazole compound represented by general formula (4), (5), (8), or (9) can be synthesized by the reaction formulas shown below with reference to synthetic examples described in The Journal of Organic Chemistry, 2007, 72 (15), 5886 and Tetrahedron, 1999, 55, p 2371.

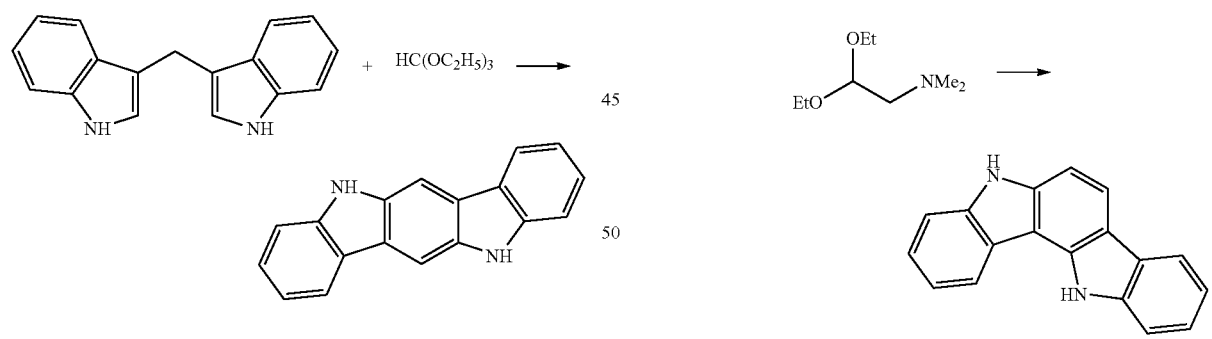

The indolocarbazole compounds prepared by the aforementioned reactions are then submitted to substitution reactions wherein the hydrogen atoms on the nitrogen atoms in the indolocarbazole skeleton are replaced by corresponding aromatic groups in the usual manner to yield the indolocarbazole compounds represented by general formulas (1) to (9).

Specific examples of the indolocarbazole compounds represented by general formulas (1) and (9) are illustrated below. However, the materials to be used in the organic electroluminescent devices of this invention are not limited thereto.

1-1
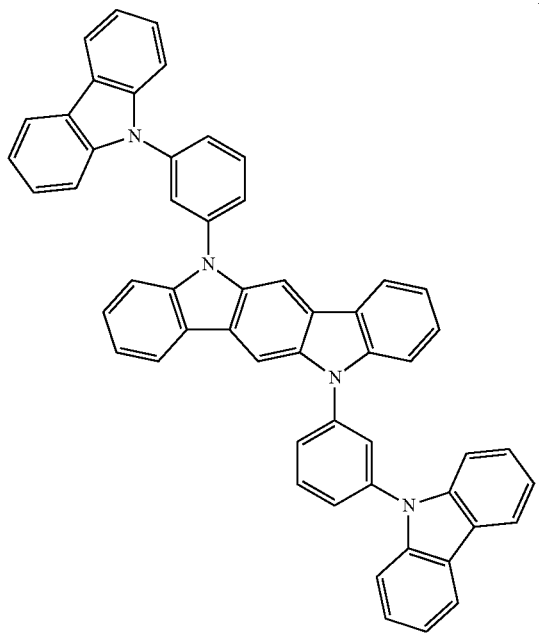
1-2
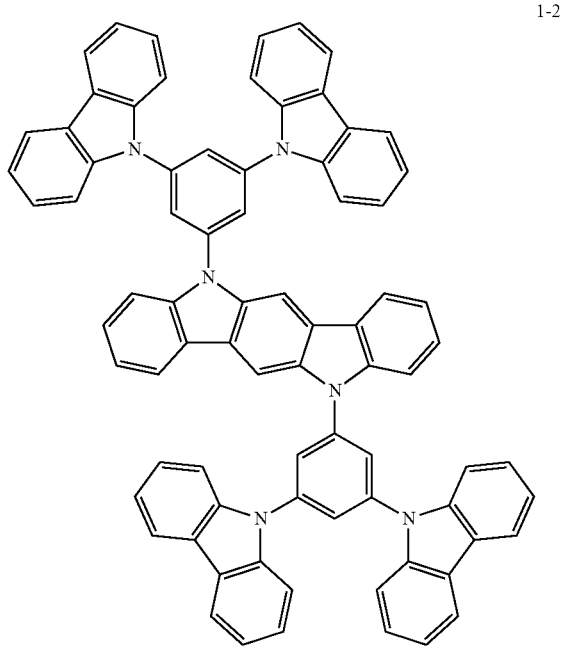
-continued
1-3
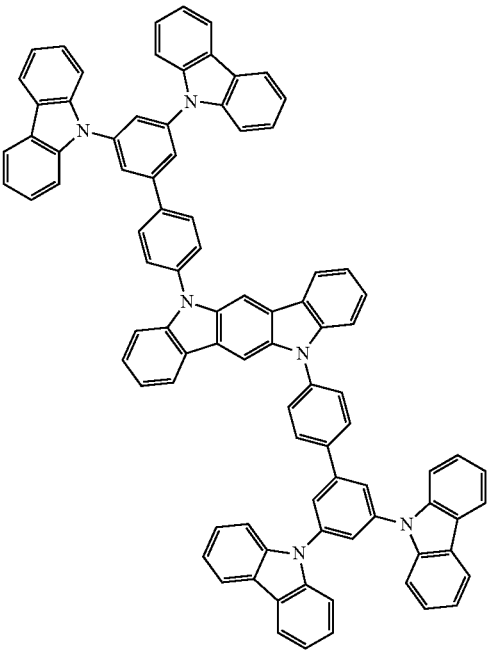
1-4

1-5
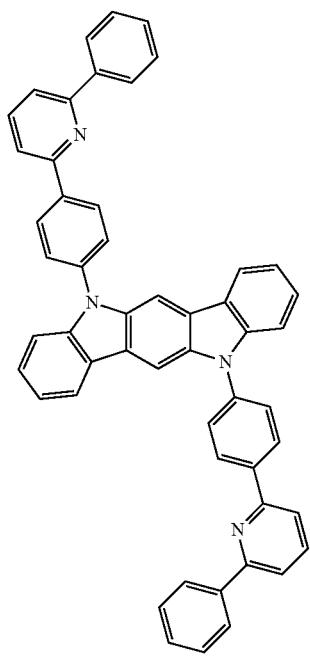
1-6
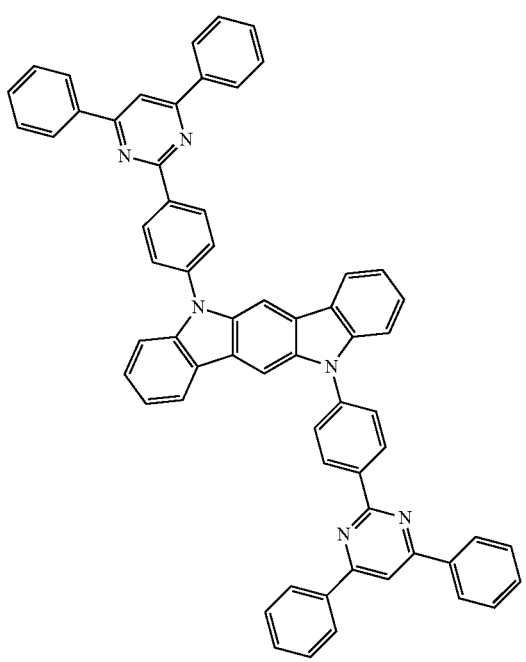
1-7
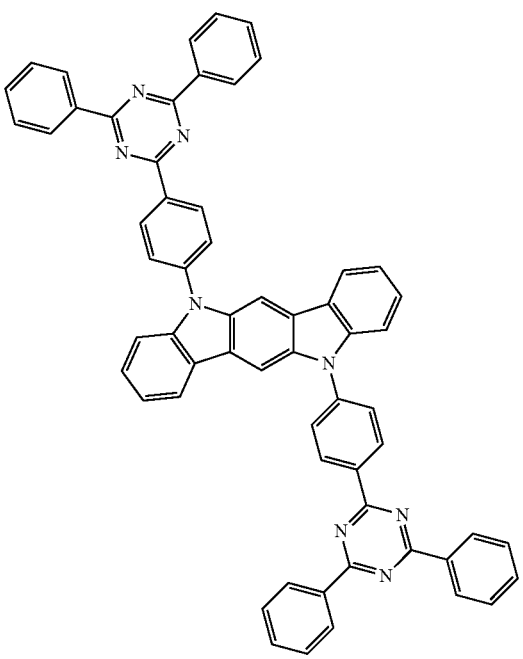
1-8
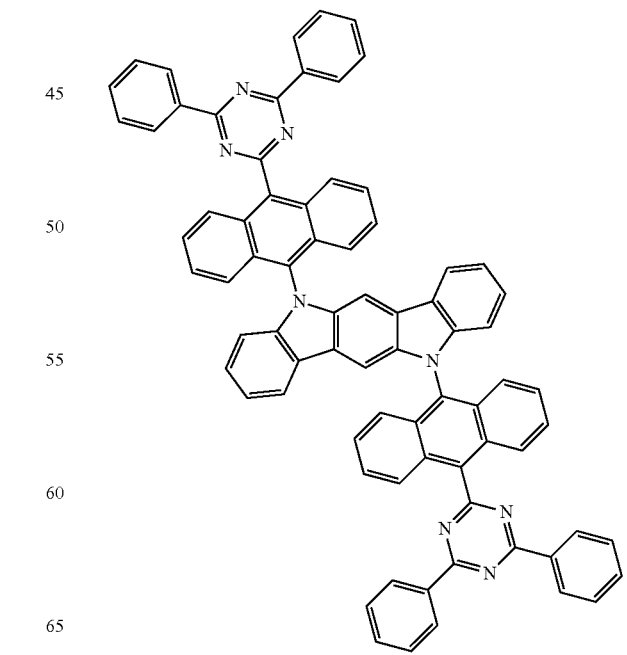

1-9
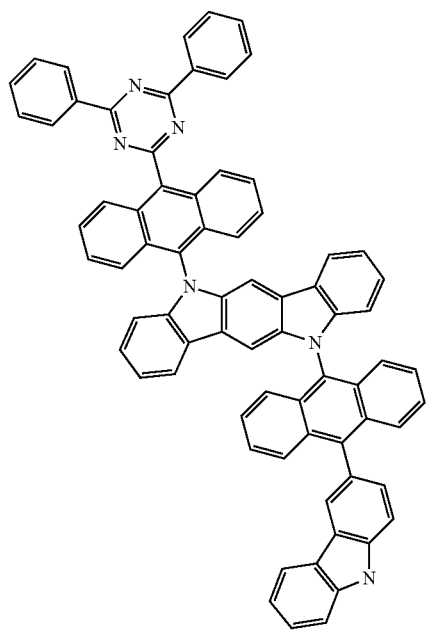
1-10
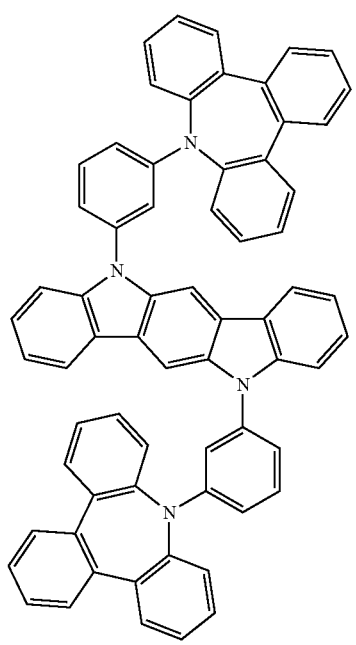
1-11
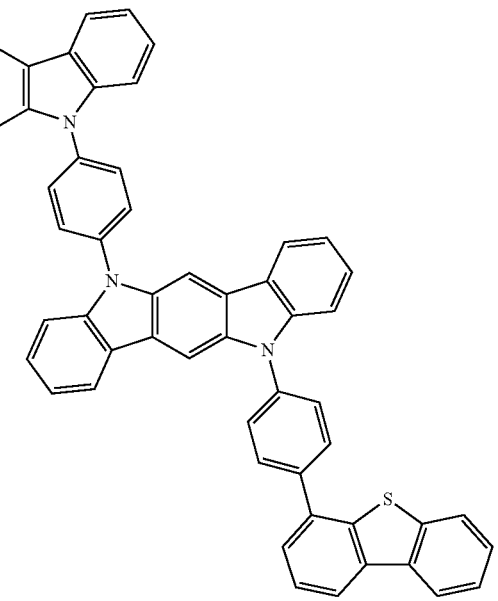
1-12
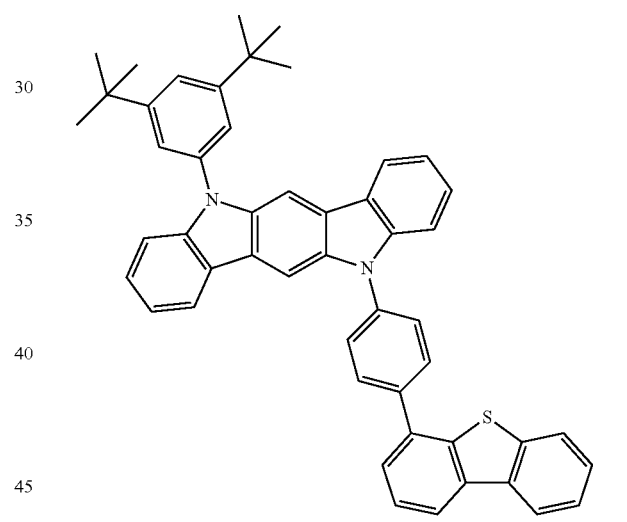
1-13
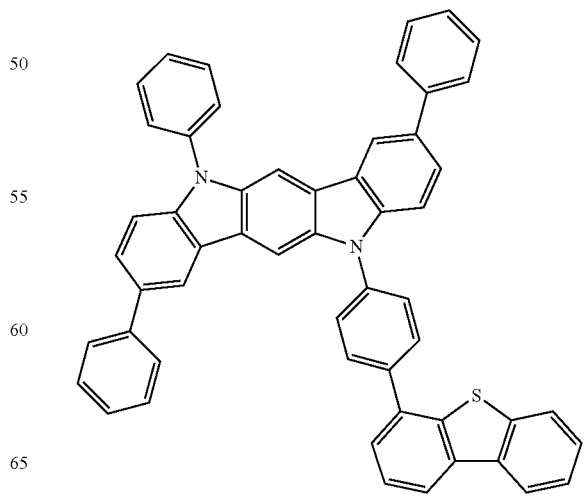

1-14
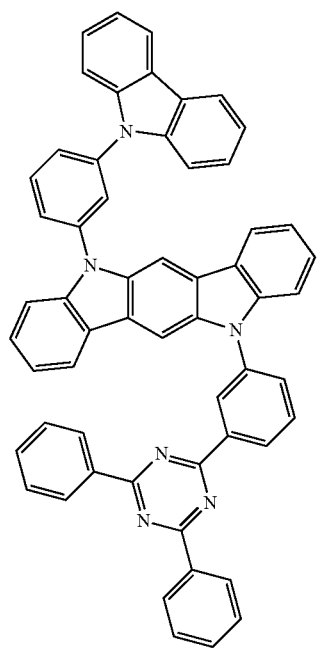
1-15
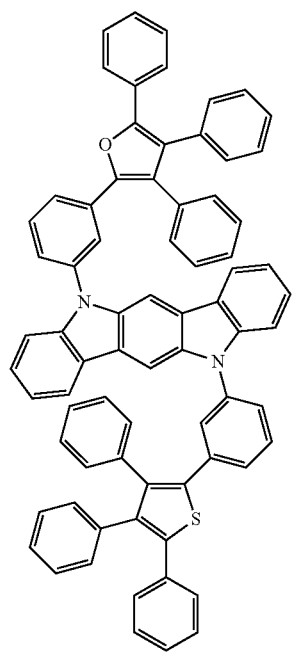
1-16
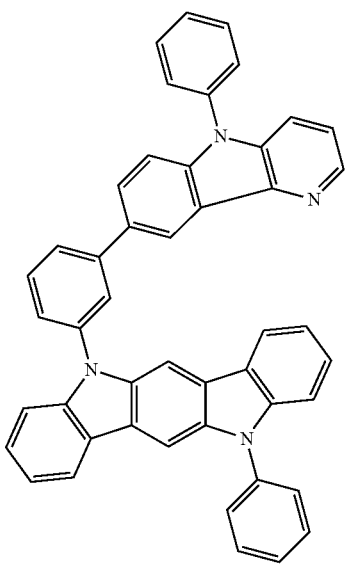
1-17
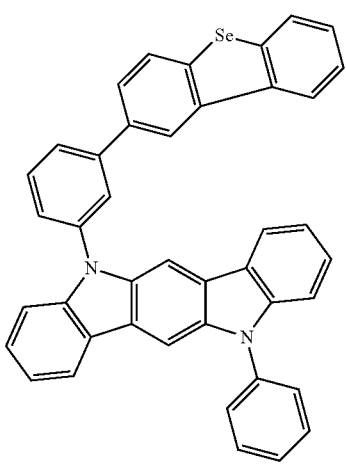
1-18
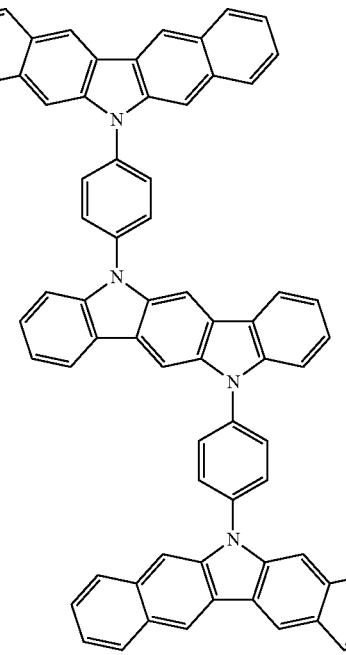

1-19
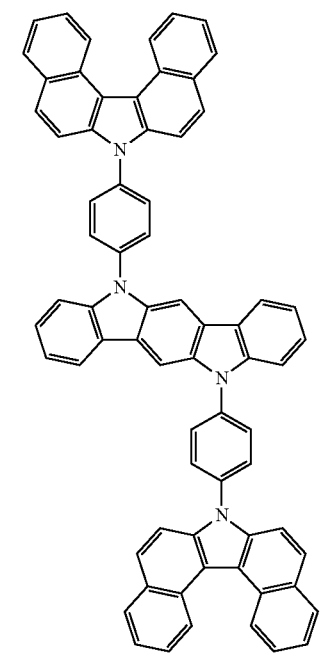
2-1
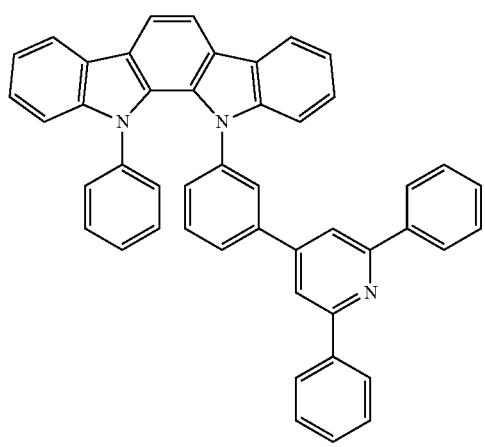
2-2
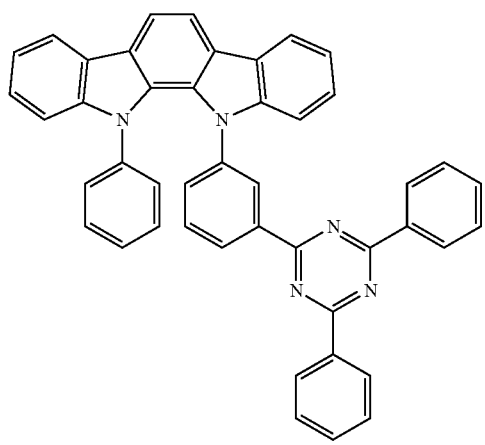
2-3
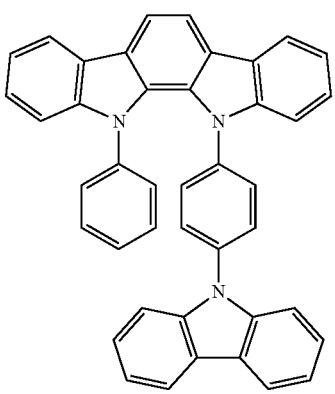
2-4
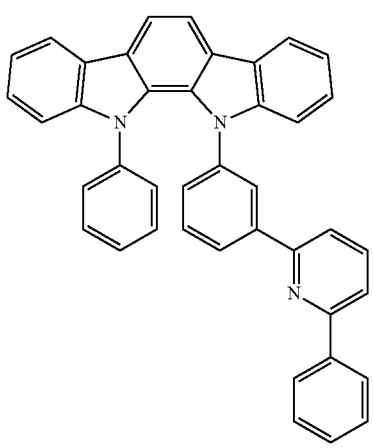
2-5
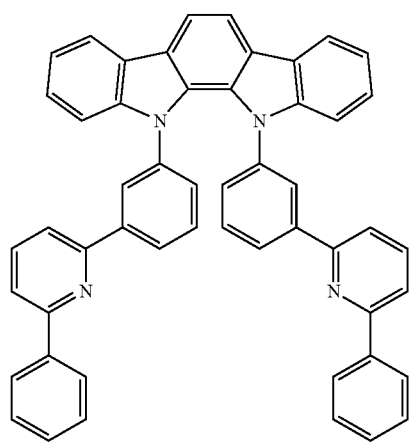

2-6
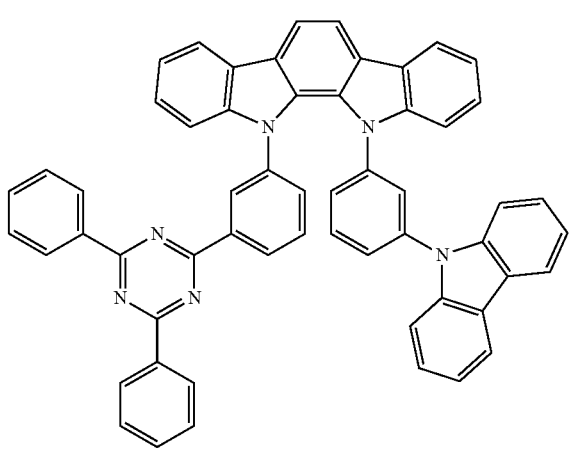
2-7
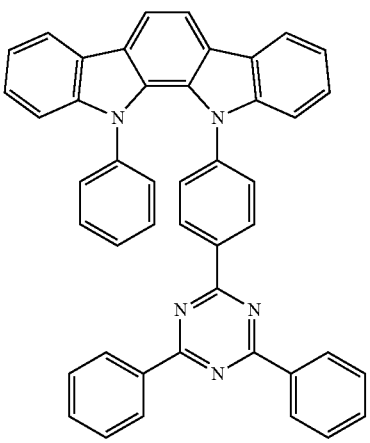
2-8
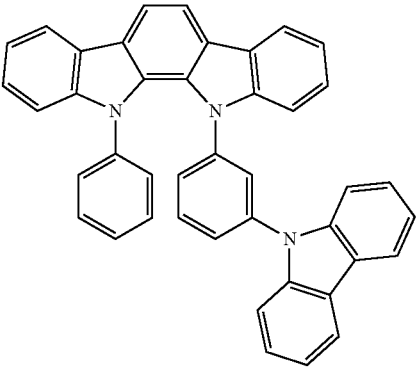
2-9
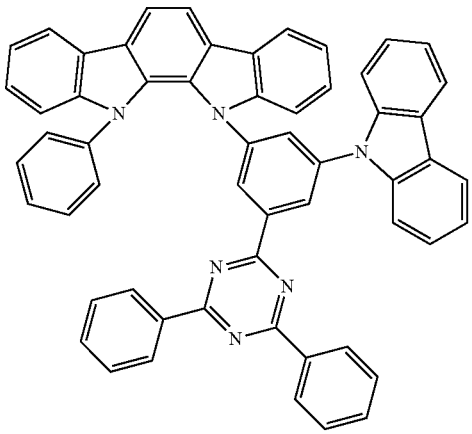
2-10
2-11
2-12
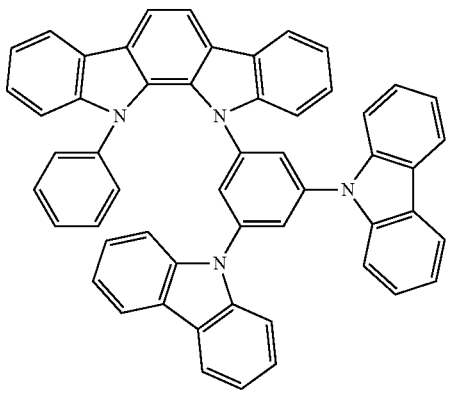

2-13
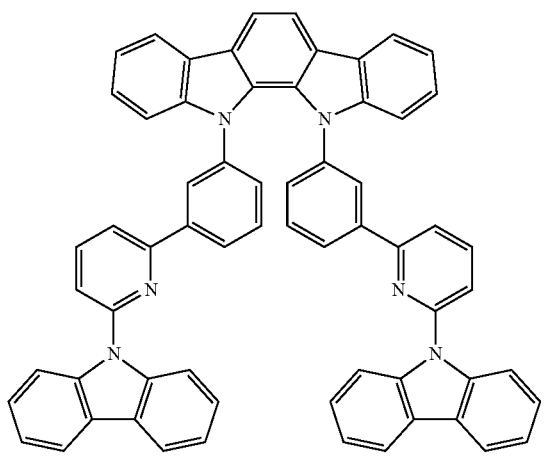
2-14
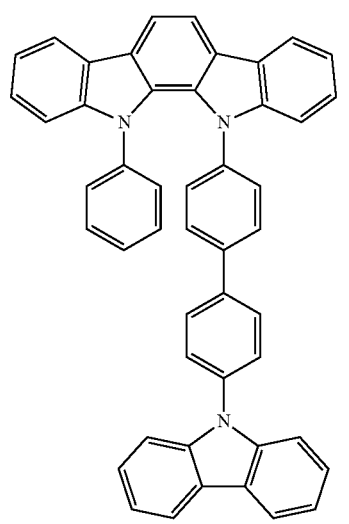
2-15
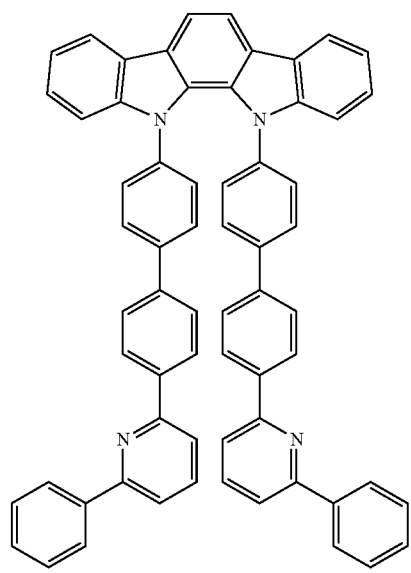
2-16
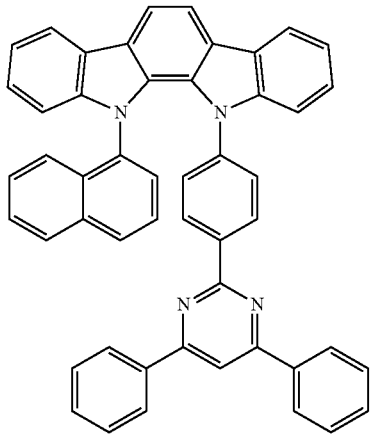
2-17
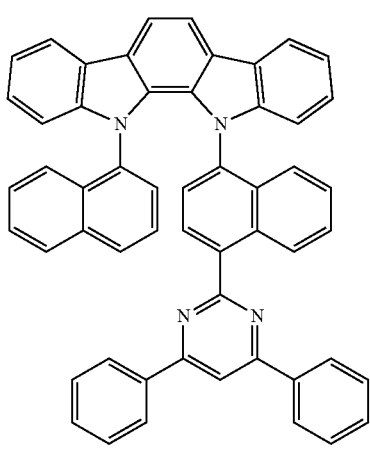
2-18
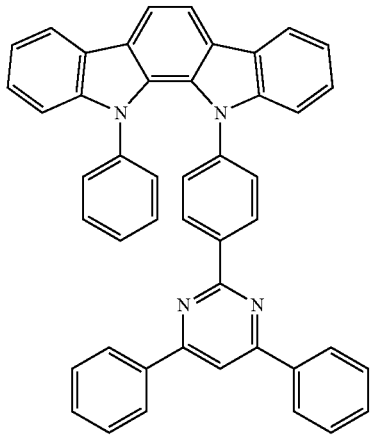

2-19
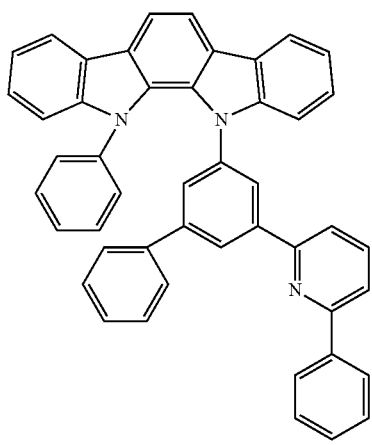
2-20
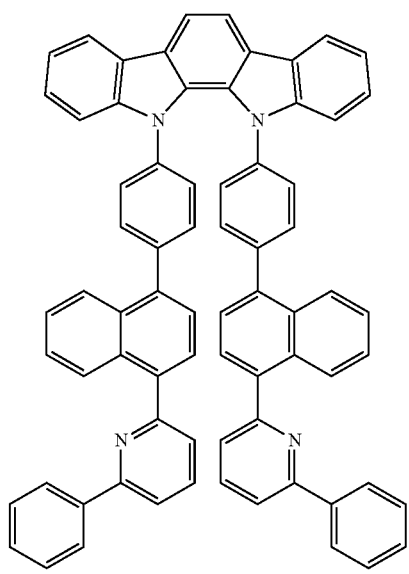
2-21
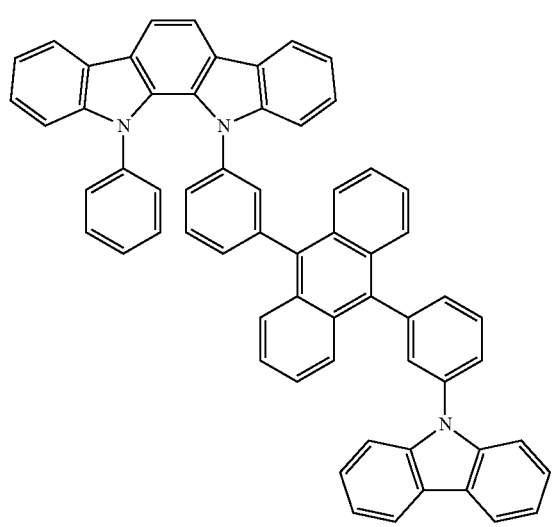
2-22
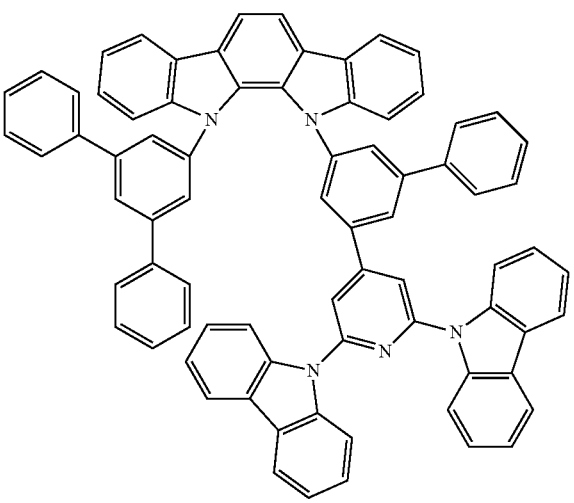
2-23
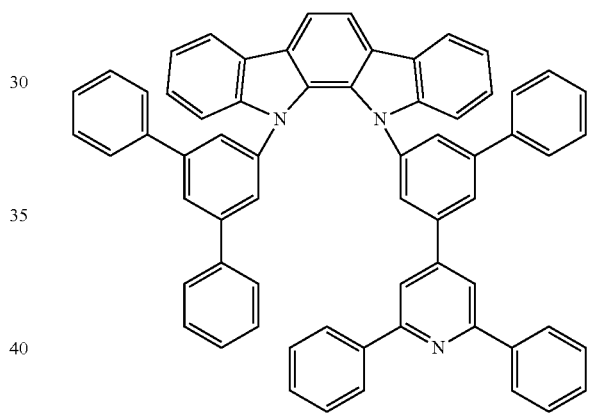
2-24
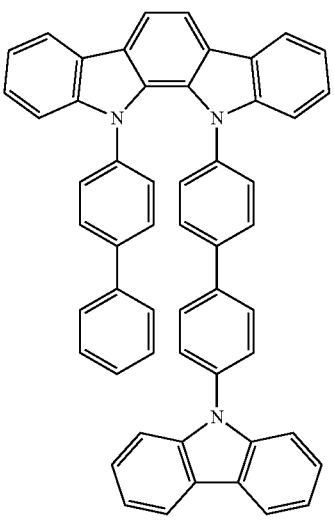

2-25
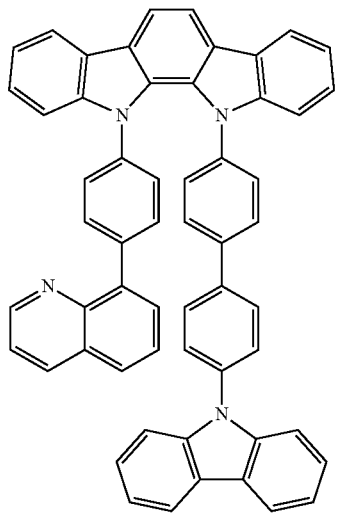
2-26
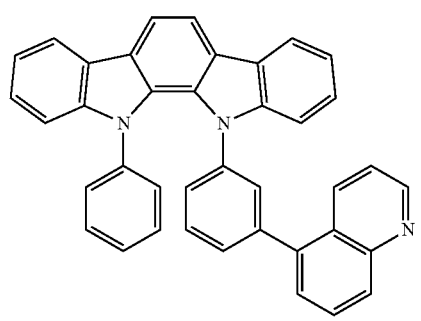
2-27
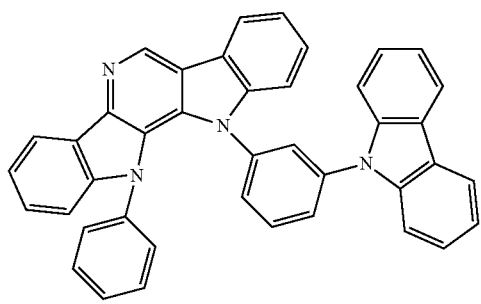
2-28
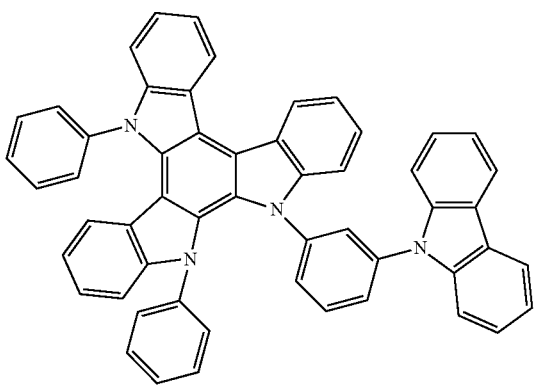
2-29
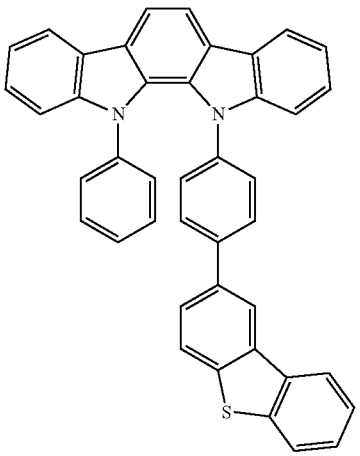
2-30
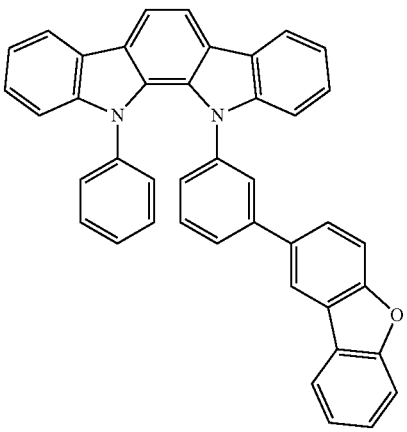
2-31
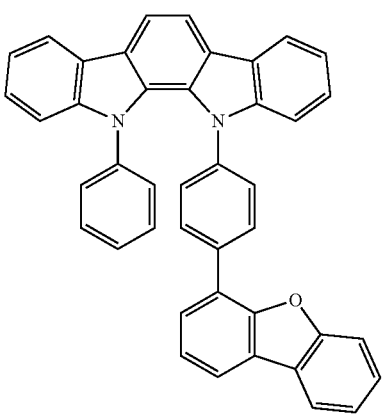

2-32
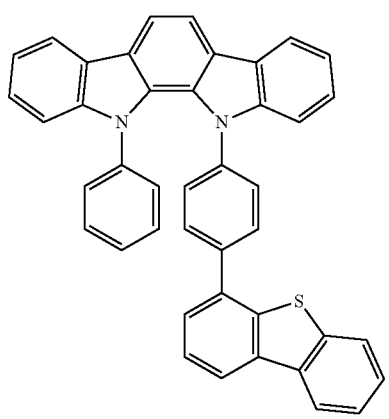
2-33
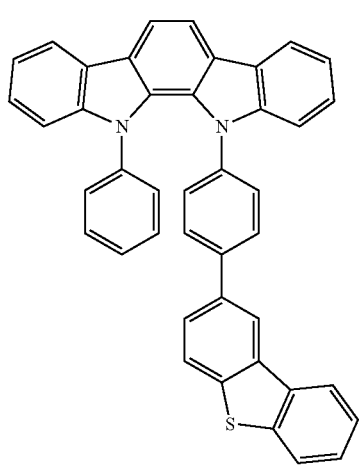
2-34
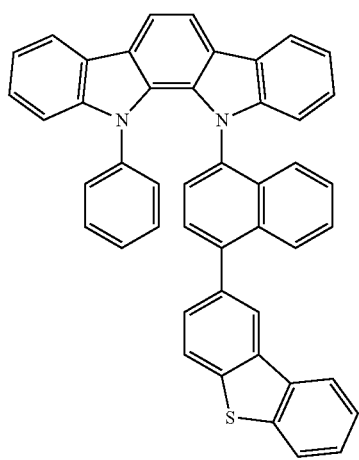
2-35
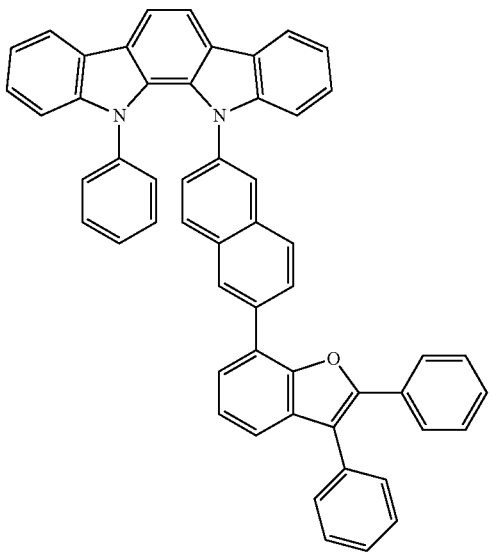
2-36
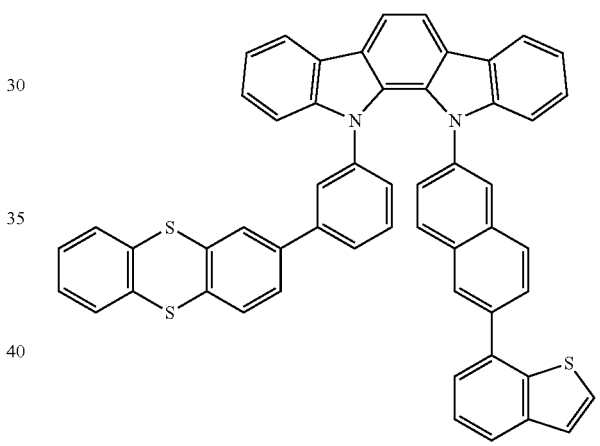
2-37
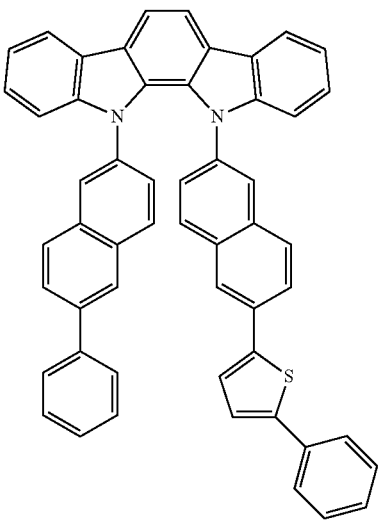

2-38
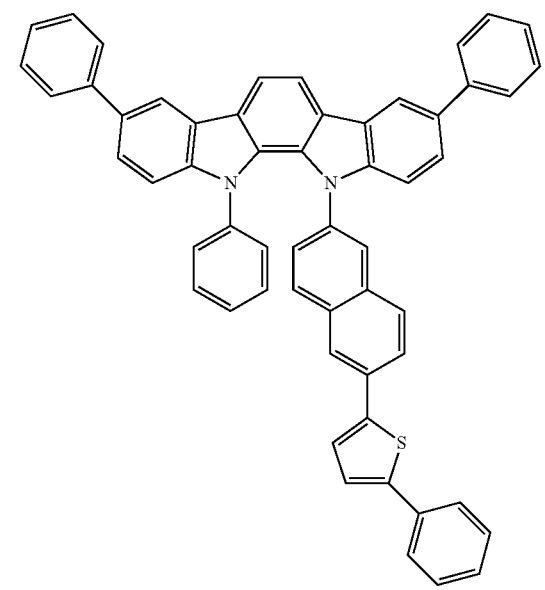
2-41
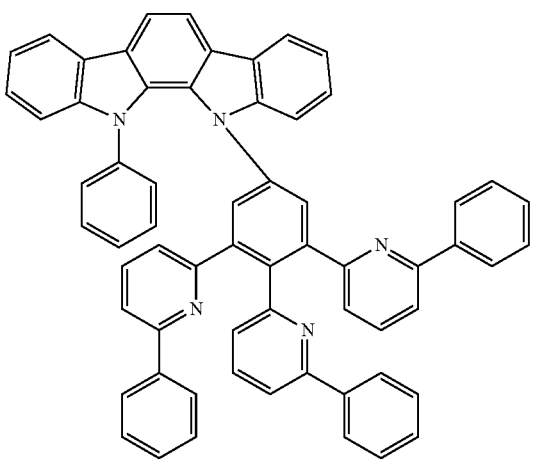
2-42
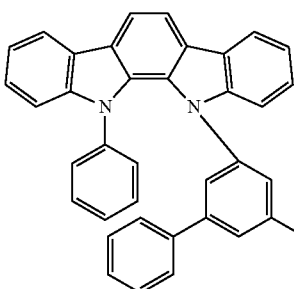
2-39
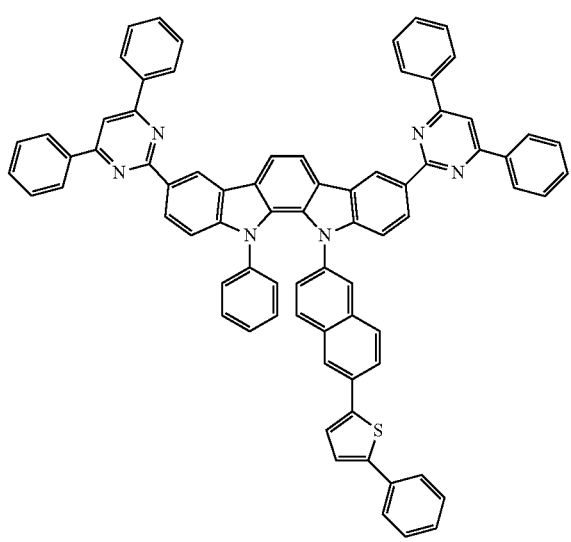
2-43
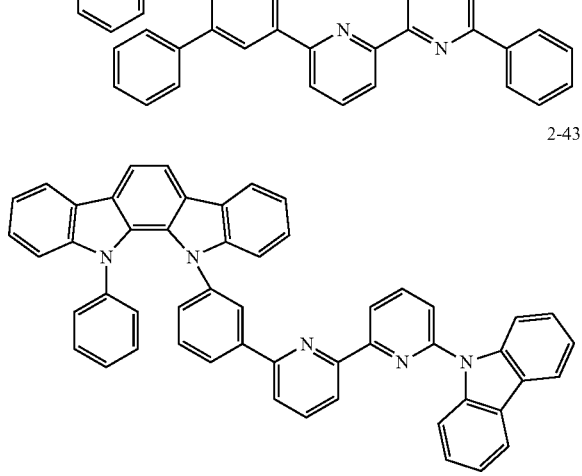
2-40
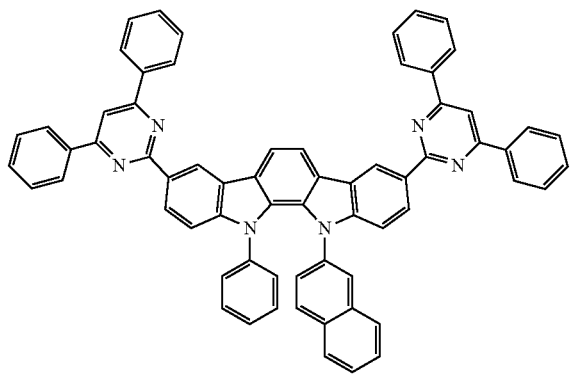
3-1
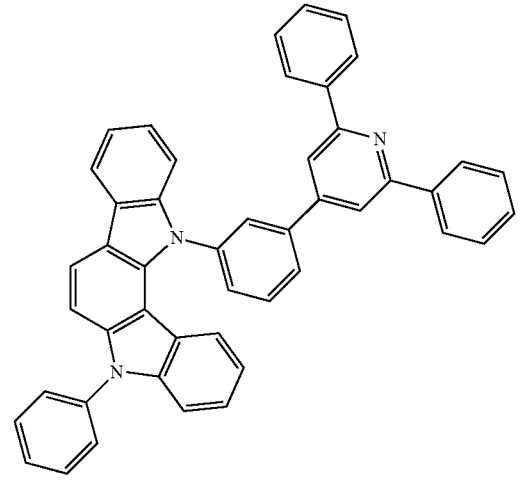

3-2
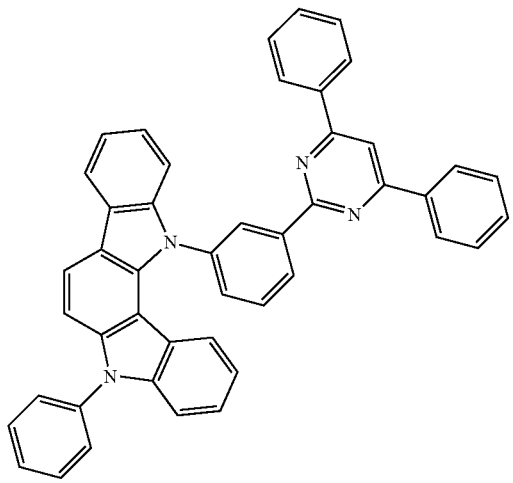
3-3
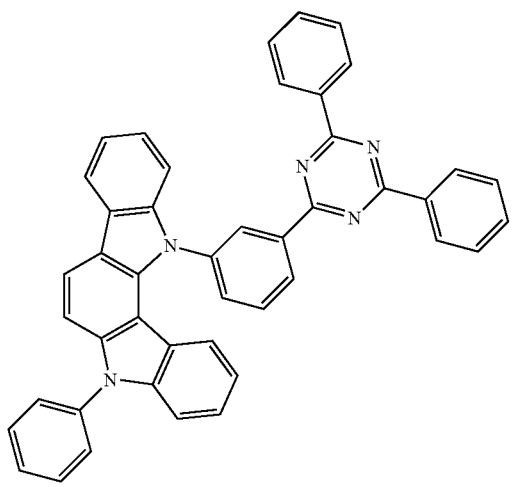
3-4
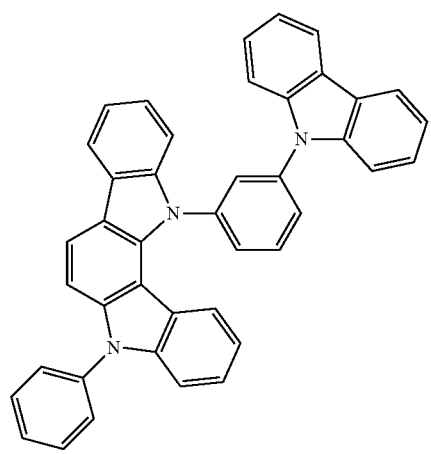
3-5
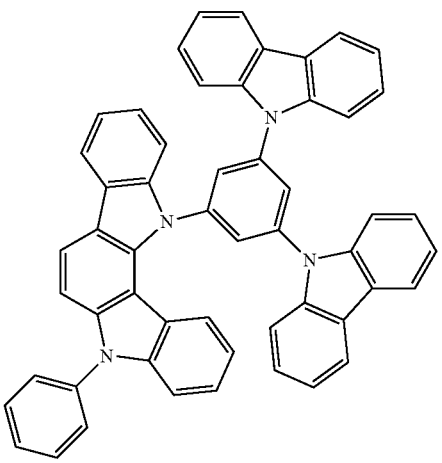
3-6
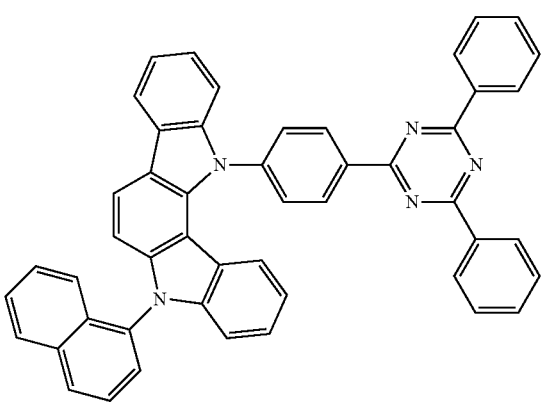
3-7
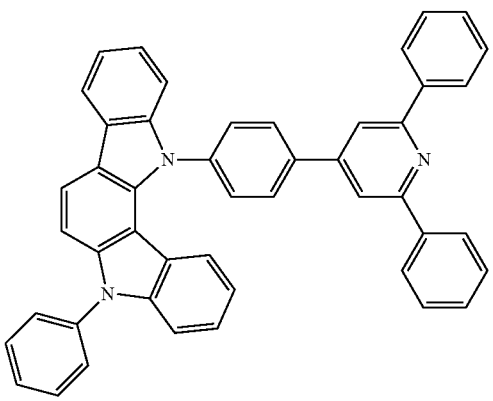

3-8
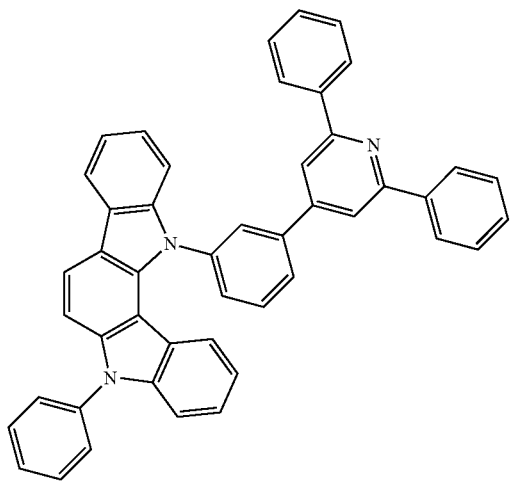
3-11
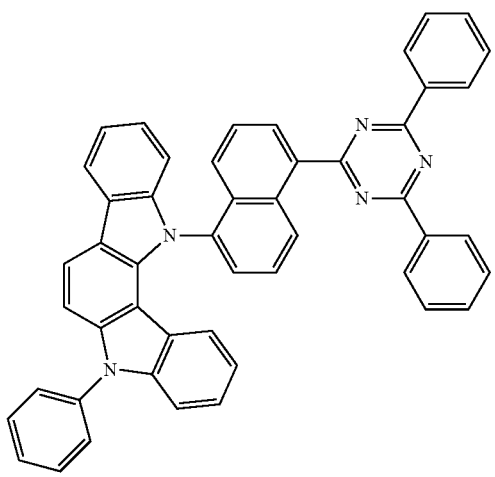
3-9
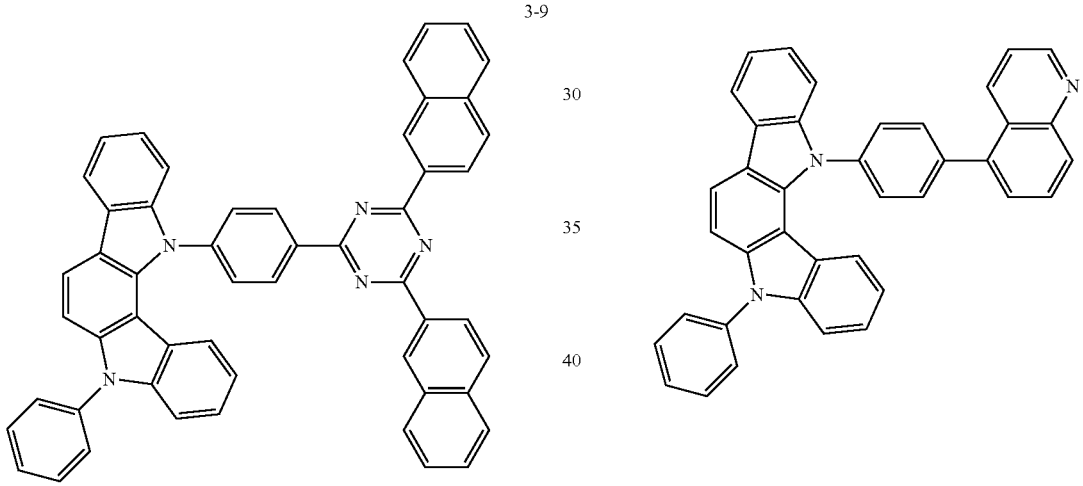
3-12
3-10
3-13
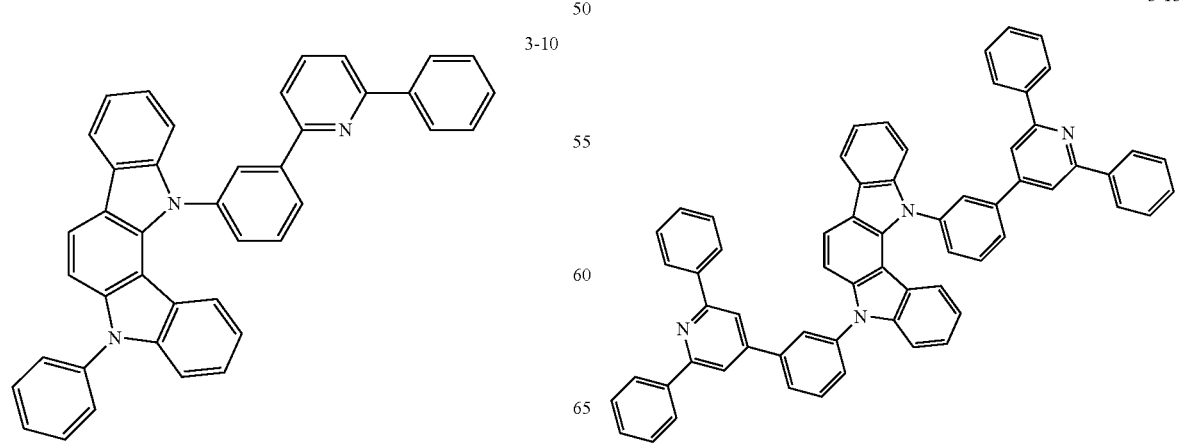

3-14
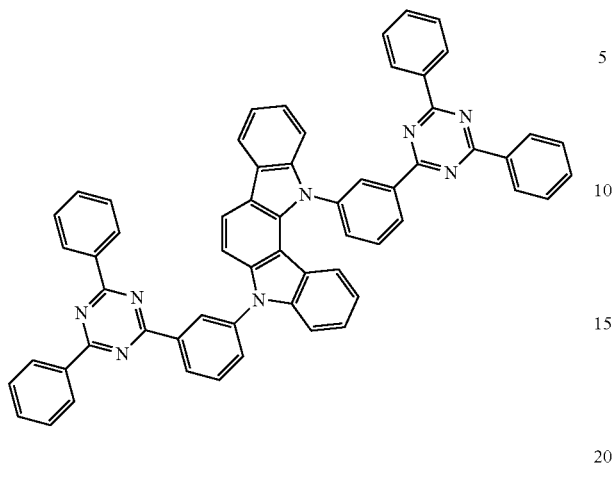
3-15
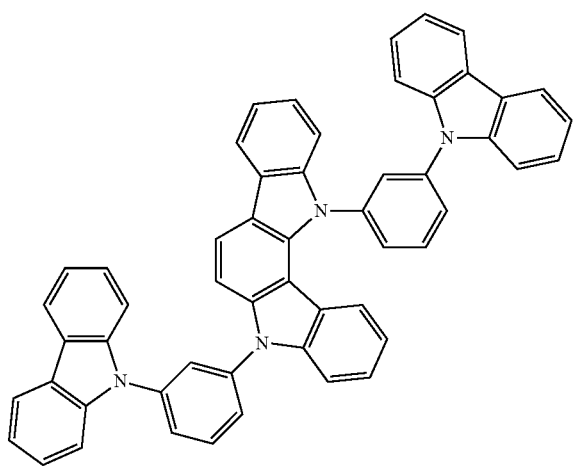
3-16
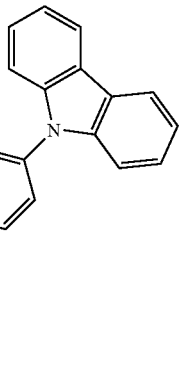
3-17
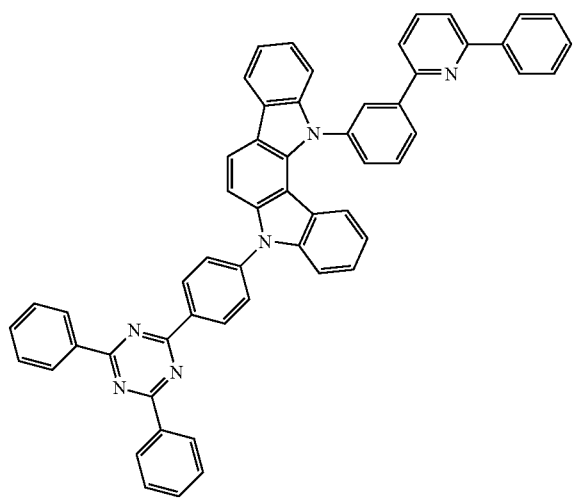
3-18
3-19

3-20
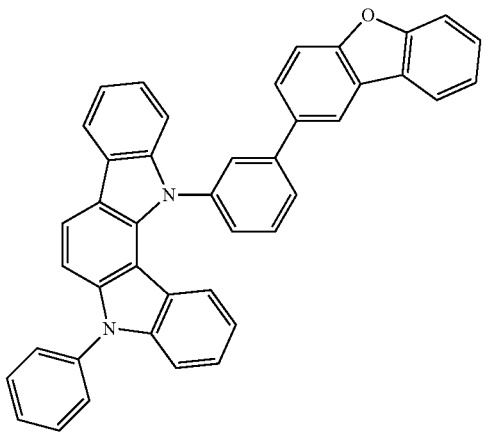
3-24
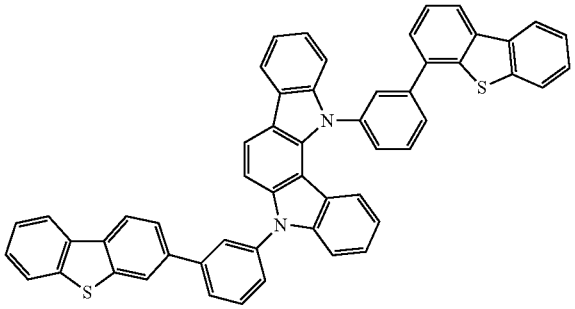
3-21
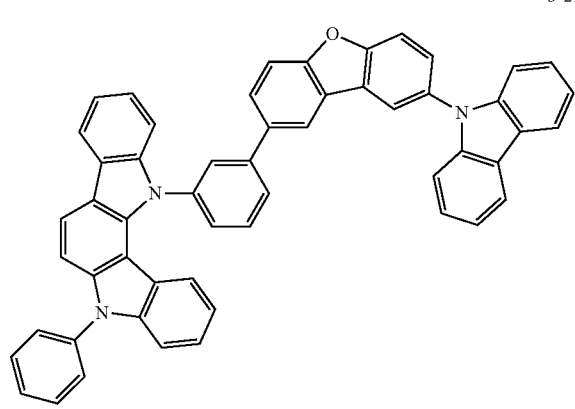
3-25
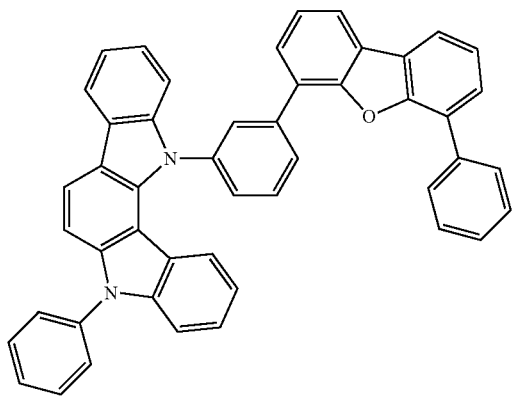
3-22
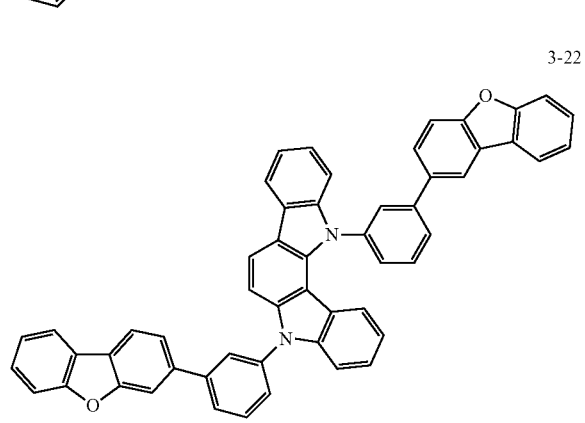
3-26
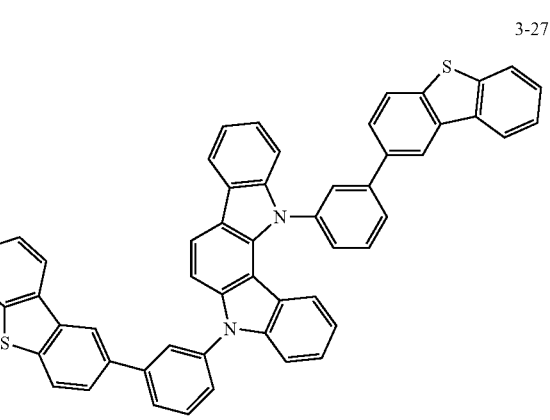
3-23
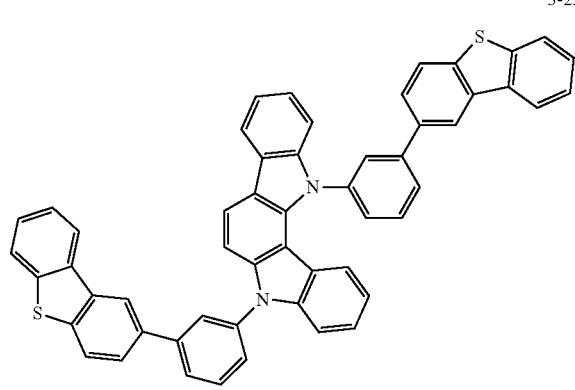
3-27

3-28
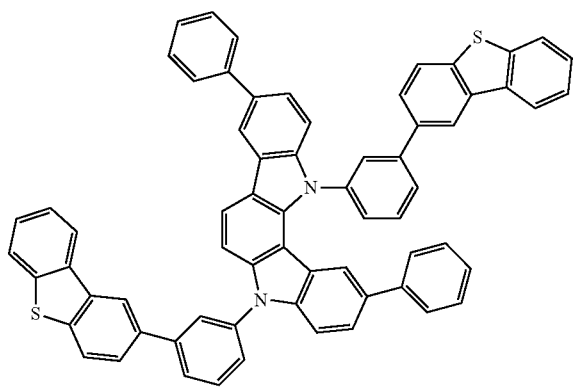
3-29
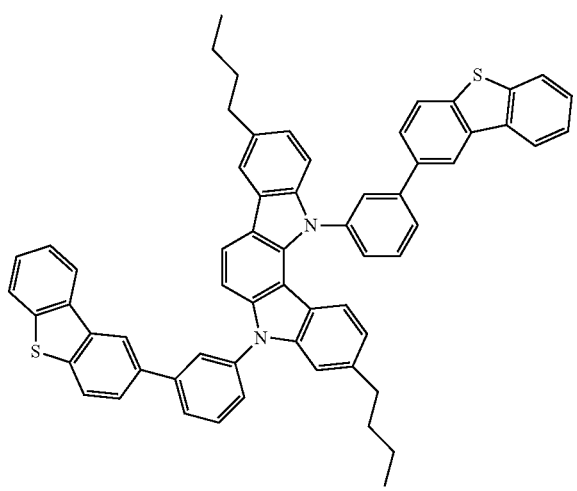
3-30
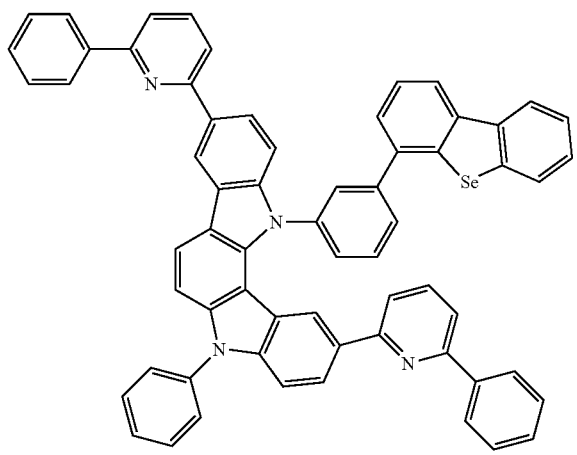
3-31
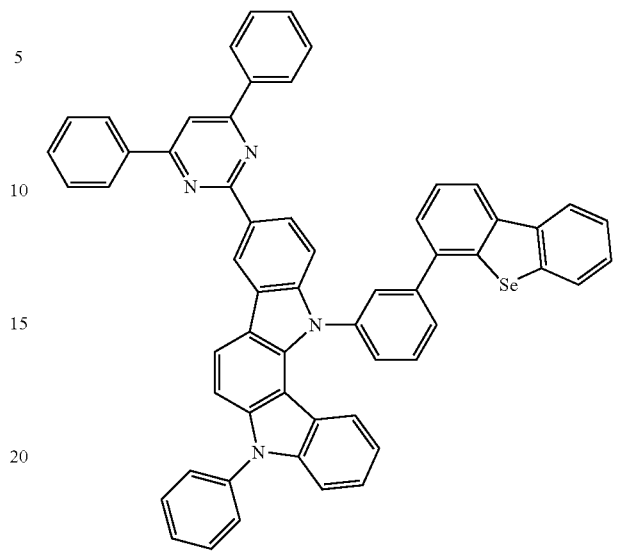
4-1
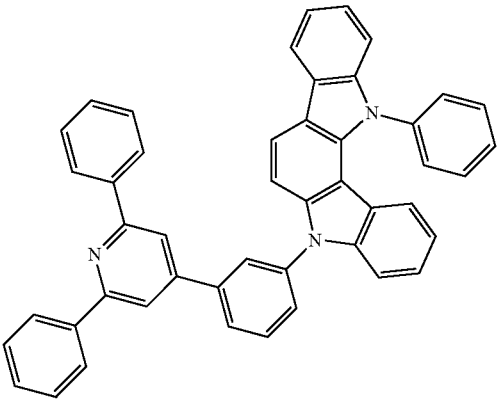
4-2
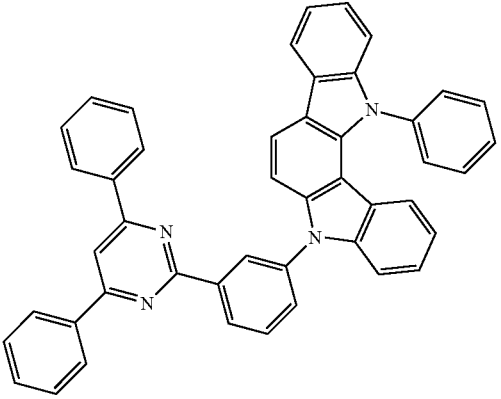

-continued
4-3
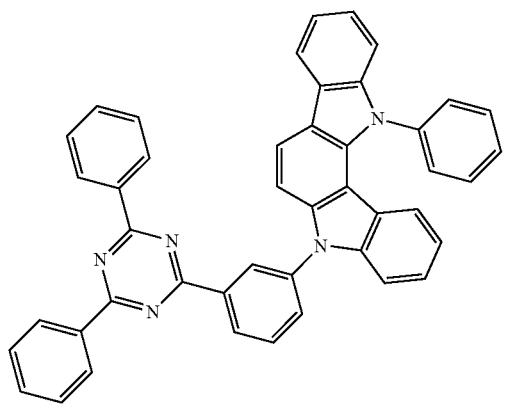
4-4
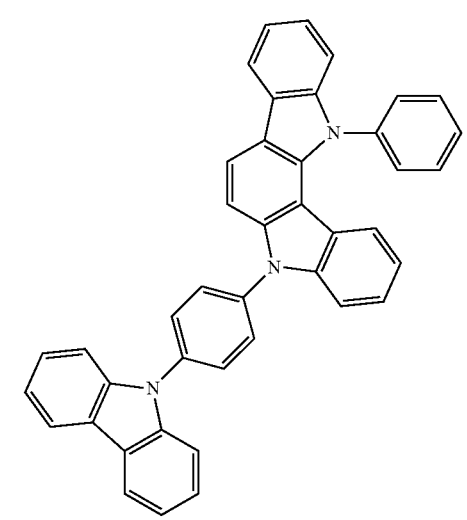
4-5
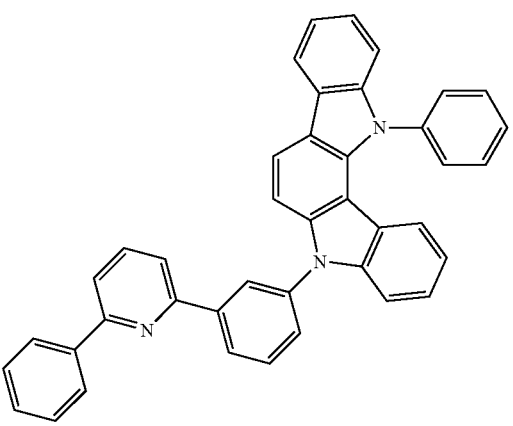
-continued
4-6
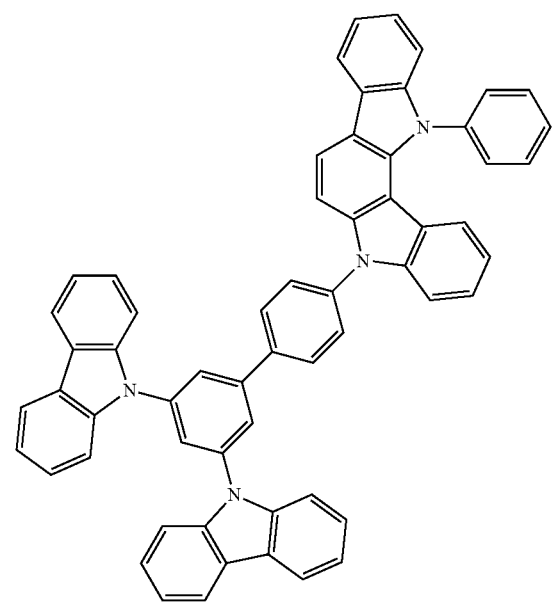
4-7
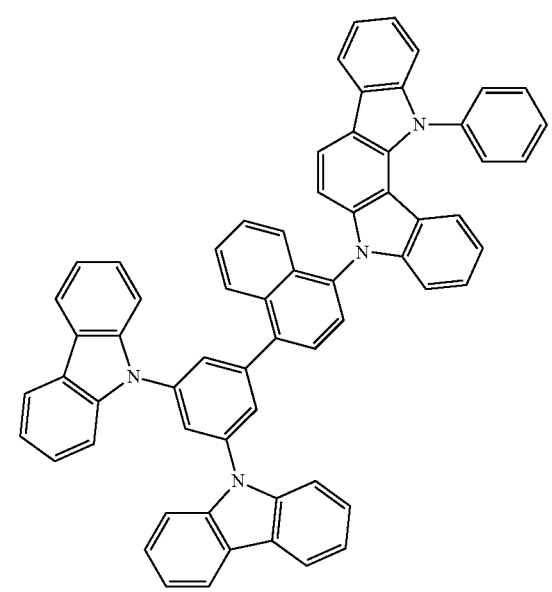
4-8
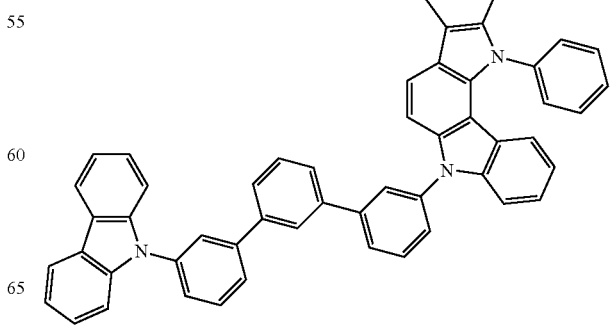

4-9
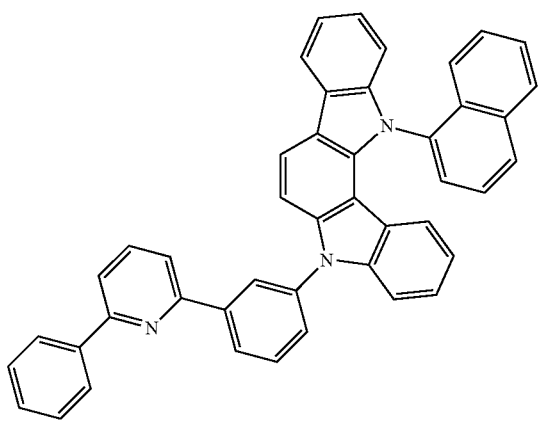
4-10
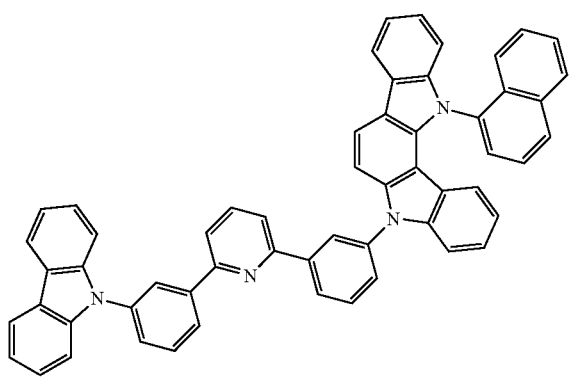
4-11
4-12
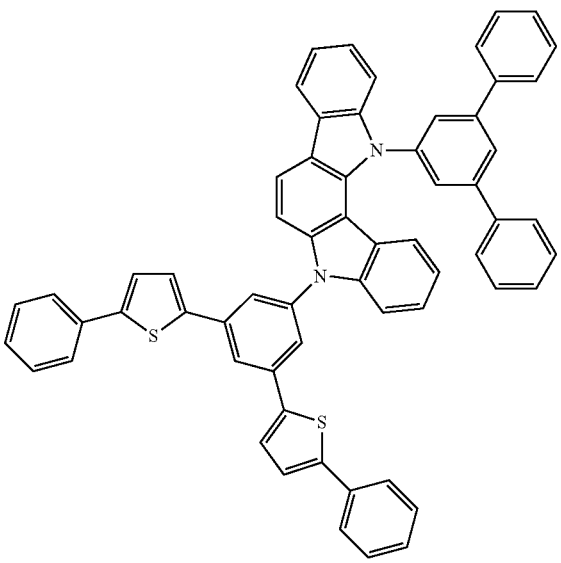
4-13
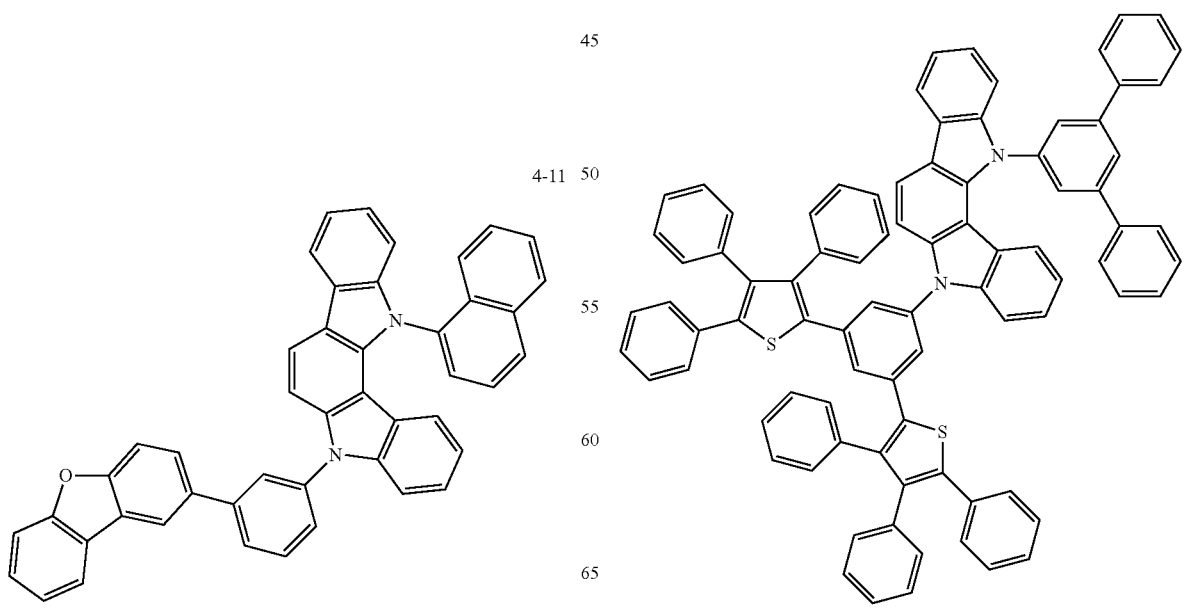

-continued
4-14
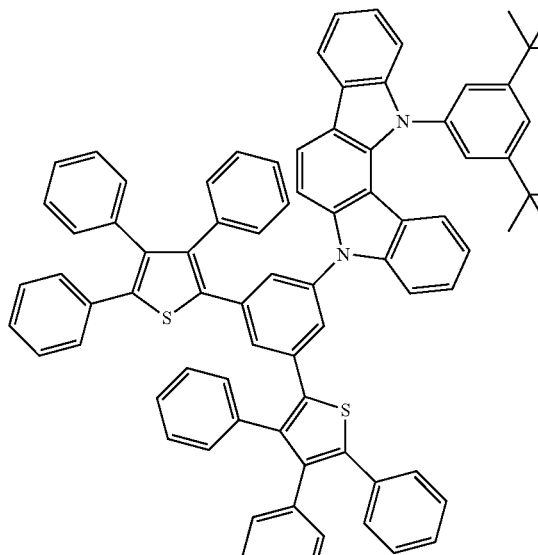
4-15
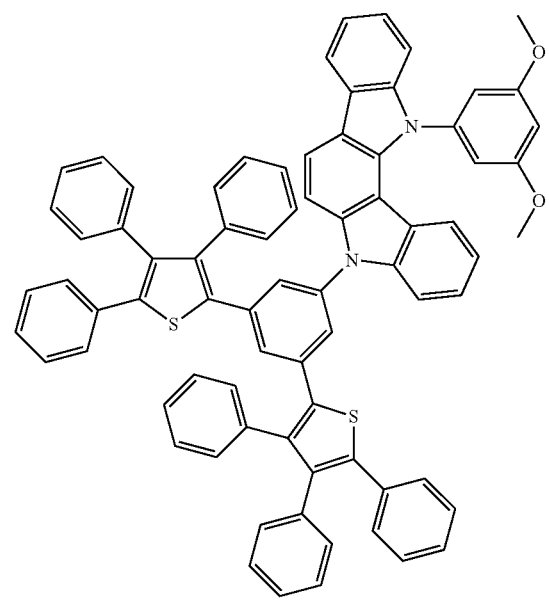
4-16
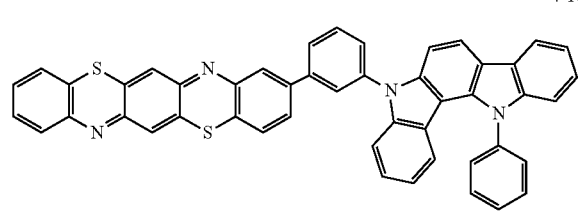
-continued
4-17
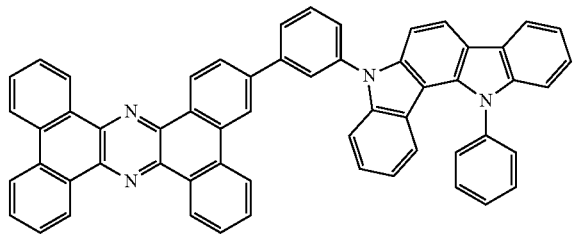
5-1
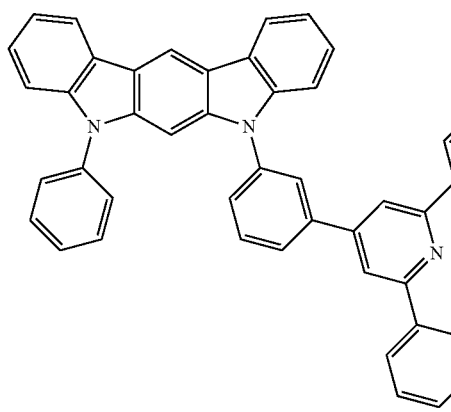
5-2
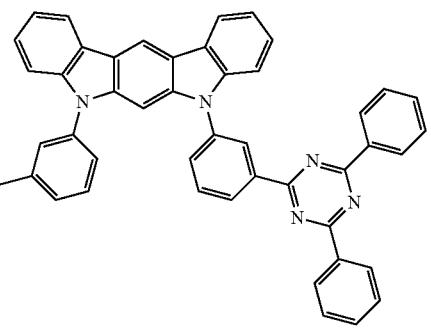
5-3
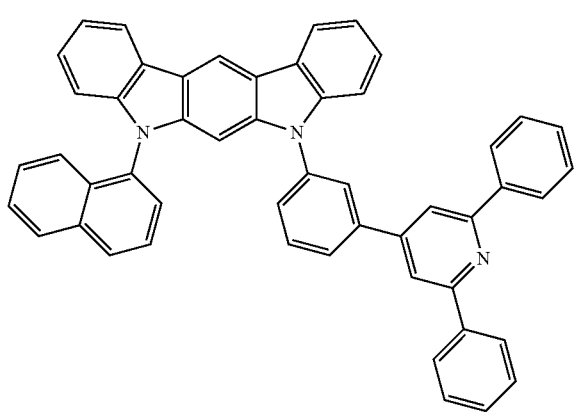

-continued
5-4
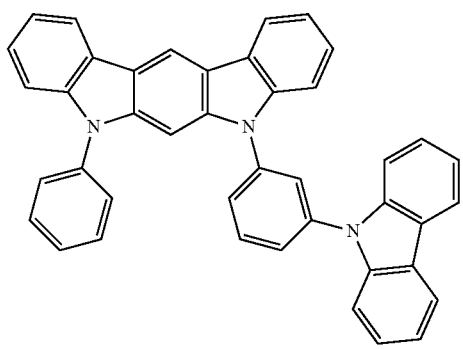
5-5
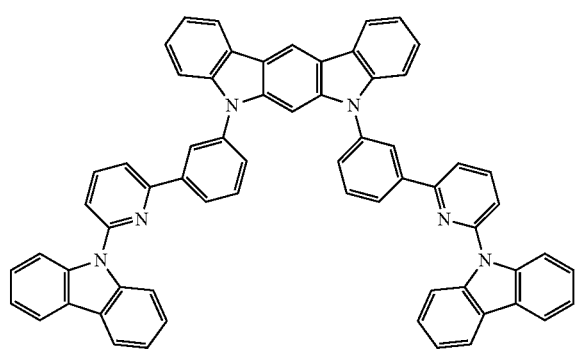
5-6
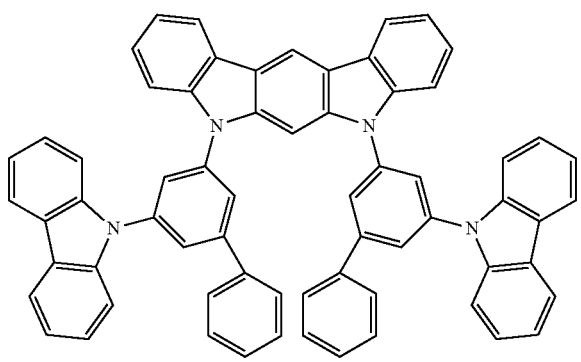
5-7
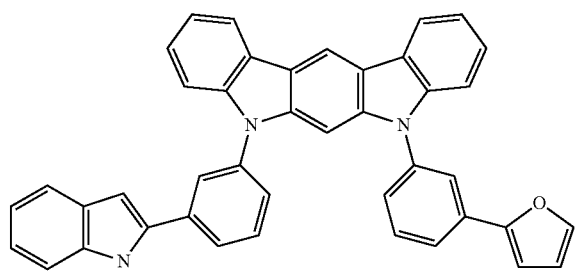
-continued
5-8
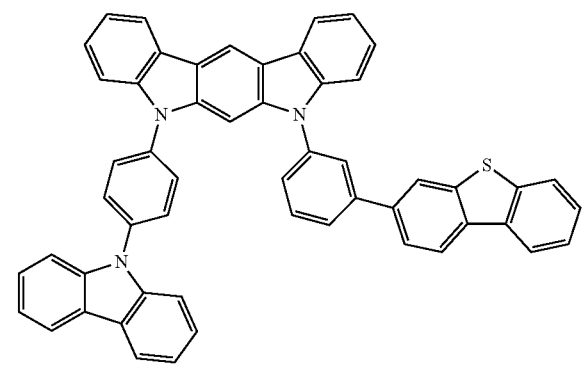
6-1
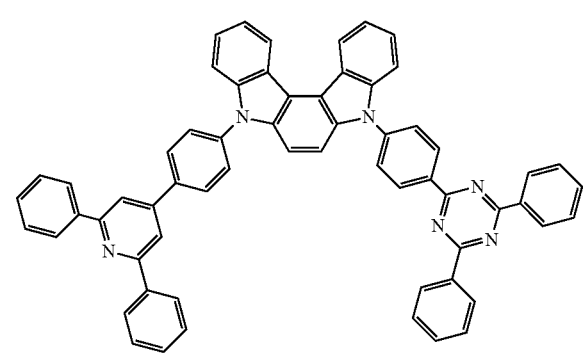
6-2
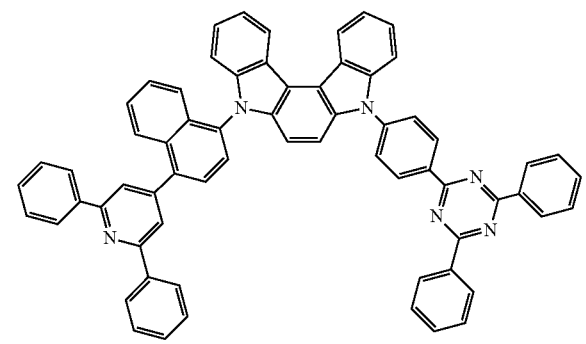
6-3
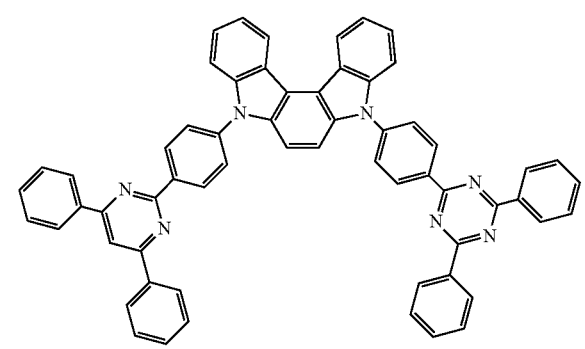

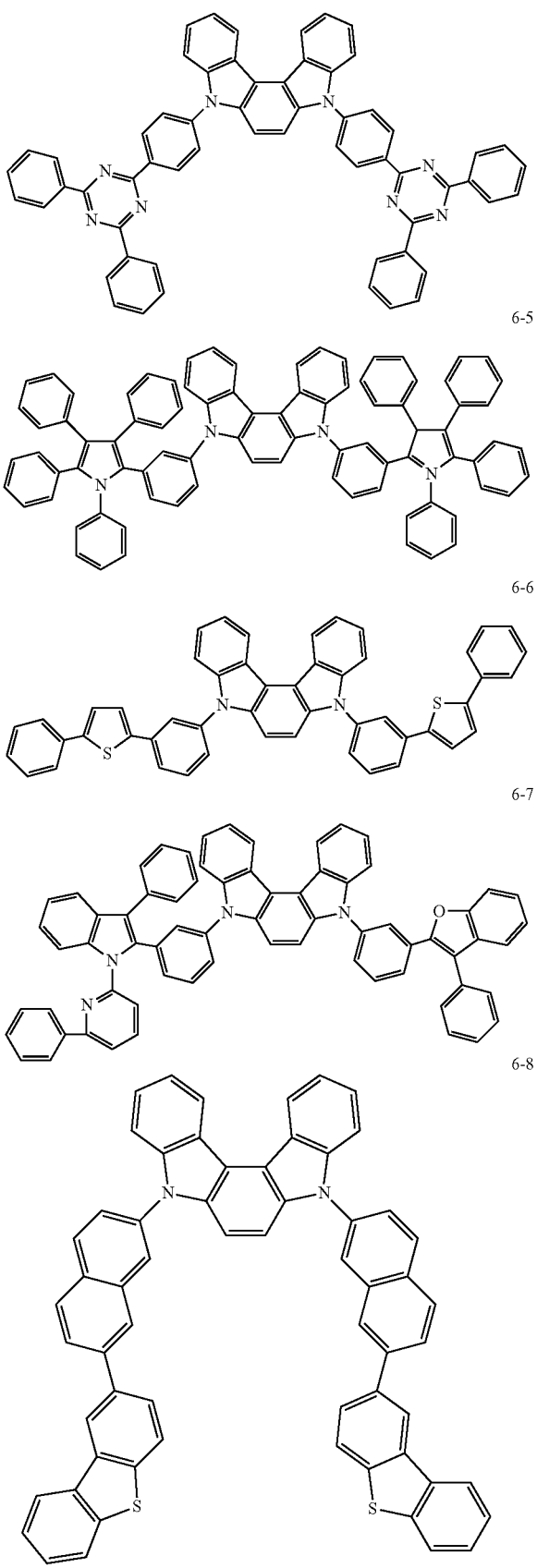

Provided that an organic EL device comprises an anode, a plurality of organic layers, and a cathode piled one upon another on a substrate, incorporation of the indolocarbazole compound represented by general formula (1) or by any of general formulas (2) to (9) (hereinafter referred to either as indolocarbazole compound of this invention or as indolocarbazole compound represented by general formula (1)) in at least one of the organic layers helps to provide an excellent organic EL device. An organic layer suitable for this purpose is a light-emitting layer, an electron-transporting layer, or a hole-blocking layer. Preferably, the indolocarbazole compound is incorporated as a host material in a light-emitting layer containing a phosphorescent dopant.

An organic EL device according to this invention is explained hereinafter.

The organic EL device of this invention comprises organic layers at least one of which comprises a light-emitting layer between an anode and a cathode piled one upon another on a substrate and, further, at least one organic layer selected from a light-emitting layer, an electron-transporting layer, and a hole-blocking layer contains the indolocarbazole compound of this invention. Advantageously, the indolocarbazole compound of this invention is contained in the light-emitting layer together with a phosphorescent dopant.

The structure of the organic EL device of this invention is explained hereinafter with reference to the drawing, but it will not be limited to the one illustrated in the drawing.

FIG. 1 schematically illustrates an example of the structure of an organic EL device generally used in this invention and the numbers in FIG. 1 stand for the following: 1 for a substrate, 2 for an anode, 3 for a hole-injecting layer, 4 for a hole-transporting layer, 5 for a light-emitting layer, 6 for an electron-transporting layer, and 7 for a cathode. The organic EL device of this invention may further comprise an exciton-blocking layer adjacent to the light-emitting layer or an electron-blocking layer between the light-emitting layer and the hole-injecting layer. The exciton-blocking layer may be inserted either on the anode side or on the cathode side of the light-emitting layer or may be inserted simultaneously on both sides. The organic EL device of this invention comprises the substrate, the anode, the light-emitting layer, and the cathode as essential layers. However, it is preferable that the device comprises a hole-injecting/transporting layer and an electron-injecting/transporting layer in addition to the essential layers and further comprises a hole-blocking layer between the light-emitting layer and the electron-injecting/transporting layer. The hole-injecting/transporting layer means a hole-injecting layer and/or a hole-transporting layer while the electron-injecting/transporting layer means an electron-injecting layer and/or an electron-transporting layer.

The organic EL device of this invention can be so constructed as to have a structure that is the reverse of the structure illustrated in FIG. 1 by piling the cathode 7, the electron-transporting layer 6, the light-emitting layer 5, the hole-transporting layer 4, and the anode 2 one upon another in this order on the substrate 1. In this case, it is also possible to add or omit a layer or layers according to the need.

—Substrate—

The organic EL device of this invention is preferably supported by a substrate. There is no specific restriction on the substrate and any of the substrates which have been used customarily in organic EL devices can be used. A substrate made from a material such as glass, transparent plastic, and quartz may be used.

—Anode—

The anode of an organic EL device is preferably made from an electrode substance having a high work function (4 eV or more) such as a metal, an alloy, an electrically conductive compound, and a mixture thereof. Specific examples of the electrode substances of this kind include metals such as Au and electrically conductive transparent materials such as CuI, indium tin oxide (ITO), $SnO_2$, and ZnO. Further, a material that is amorphous and formable into a transparent electrically conductive film such as IDIXO ($In_2O_3$—ZnO) may be used. The anode may be formed by preparing a thin film from any of those electrode substances by a method such as vapor deposition and sputtering and then forming a pattern of desired shape on the thin film by photolithography. Or, in the case where high accuracy is not required in patterning (100 μm or more), a pattern may be formed through a mask of desired shape during vapor deposition or sputtering of the aforementioned electrode substance. In the case where a substance that is applicable by a coating method such as an electrically conductive organic compound is used, a wet film-forming process such as printing and coating may be employed. When emitted light is taken out from the anode, the transmittance is desirably set at 10% or more and the sheet resistance as the anode is preferably several hundred Ω/□ or less. Further, the thickness of the film is normally selected from the range of 10 to 1,000 nm, preferably 10 to 200 nm, although it varies with the film-forming material.

—Cathode—

Meanwhile, the cathode is made from an electrode substance having a low work function (4 eV or less) such as a metal (hereinafter referred to as electron-injecting metal), an alloy, an electrically conductive compound, and a mixture thereof. Specific examples of the electrode substances of this kind include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. From the viewpoint of electron-injecting property and durability against oxidation and the like, a mixture of an electron-injecting metal and a second metal which is higher in work function and more stable than the electron-injecting metal is suitable for use as an electrode substance and examples thereof include a magnesium/silver mixture, a magnesium/aluminum mixture, a magnesium/indium mixture, an aluminum/aluminum oxide ($Al_2O_3$) mixture, a lithium/aluminum mixture, and aluminum. The cathode is formed by preparing a thin film from any of those electrode substances by a method such as vapor deposition and sputtering. The sheet resistance as the cathode is preferably several hundred Ω/□ or less and the thickness of the film is selected from the range of 10 nm to 5 μm, preferably 50 to 200 nm. Making either the anode or the cathode of an organic EL device transparent or translucent in order to transmit emitted light advantageously improves the luminance.

A transparent or translucent cathode may be made by forming a cathode with a film thickness of 1 to 20 nm from the aforementioned metal and then forming thereon a film of one of the electrically conductive transparent materials described above in explanation of the anode. This method can be applied to fabricate a device in which both the anode and the cathode display good transmittance properties.

—Light-Emitting Layer—

The light-emitting layer is a phosphorescent light-emitting layer and contains a phosphorescent dopant and a host material. Examples of the phosphorescent dopant include an organic metal complex containing at least one metal selected from ruthenium, rhodium, palladium, silver, rhenium, osmium, iridium, platinum, and gold. The organic metal complexes of this kind are known in the aforementioned prior art technical documents and elsewhere and a suitable organic metal complex may be selected from them and used.

Preferable examples of the phosphorescent dopant include a complex containing a noble metal element such as Ir in the center, typically Ir(ppy)$_3$, a complex such as (Bt)$_2$Iracac, and a complex such as (Btp)Ptacac. Specific examples of those complexes are illustrated below, but the complexes useful for this invention are not limited thereto.

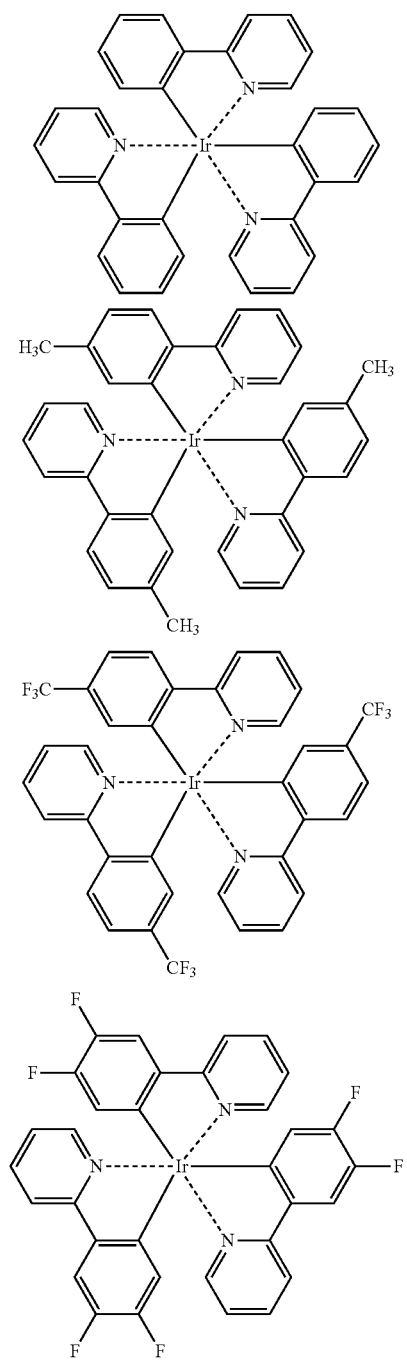

-continued
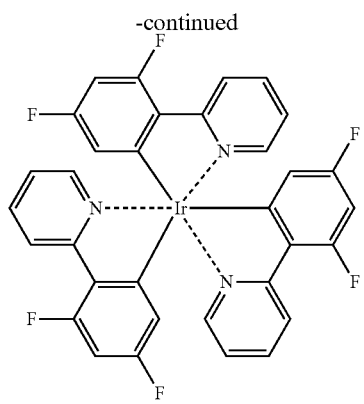
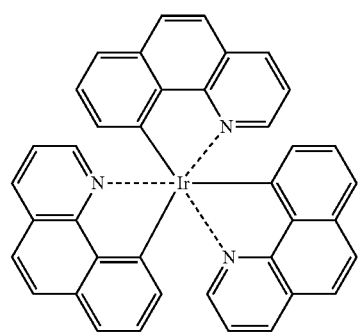
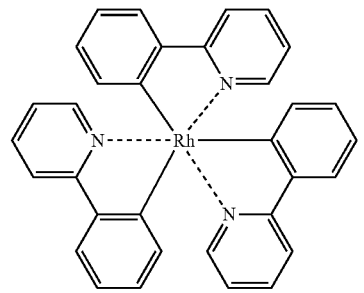
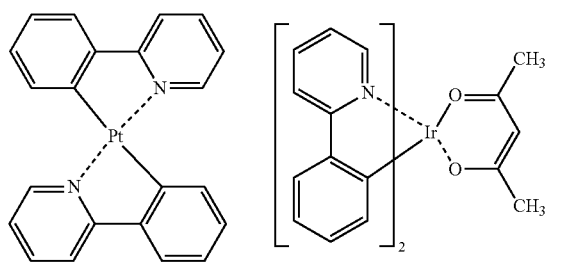
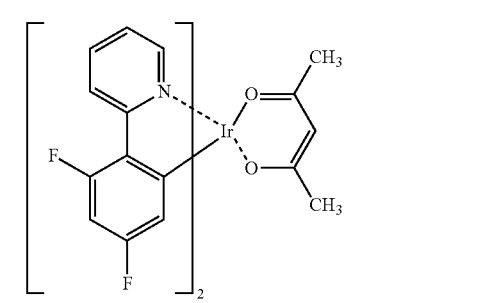
-continued
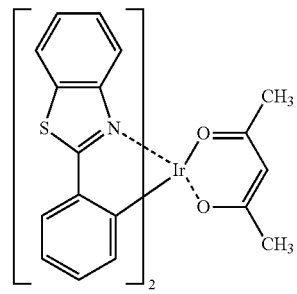
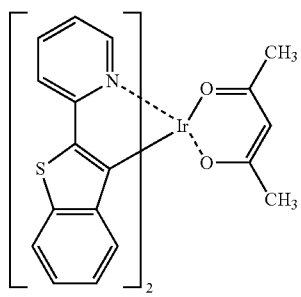
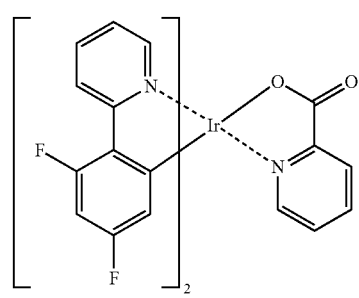
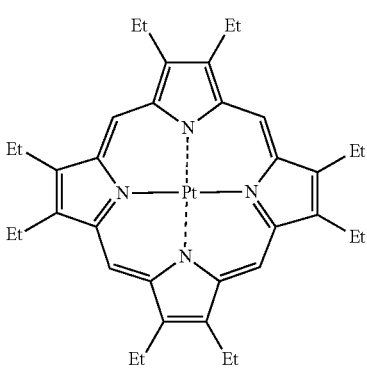
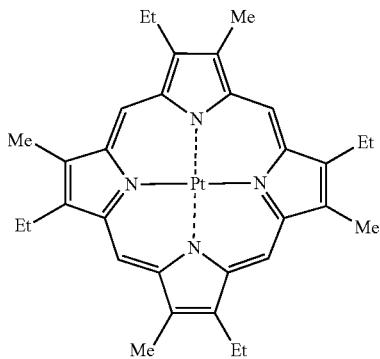

-continued

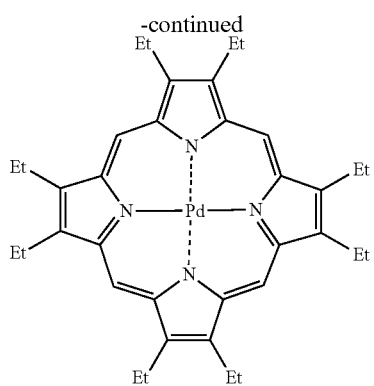

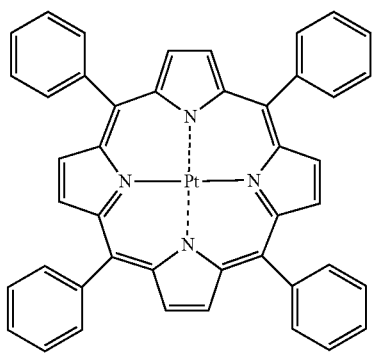

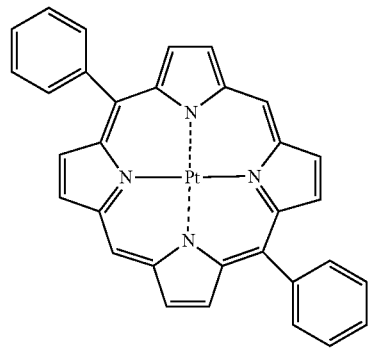

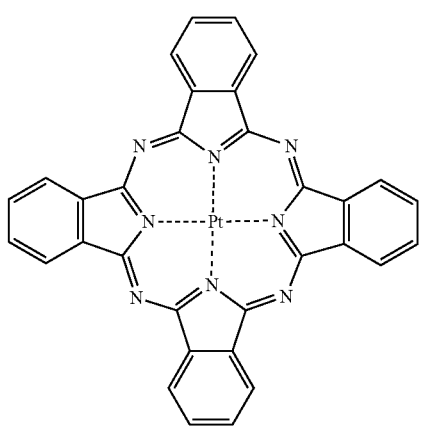

-continued

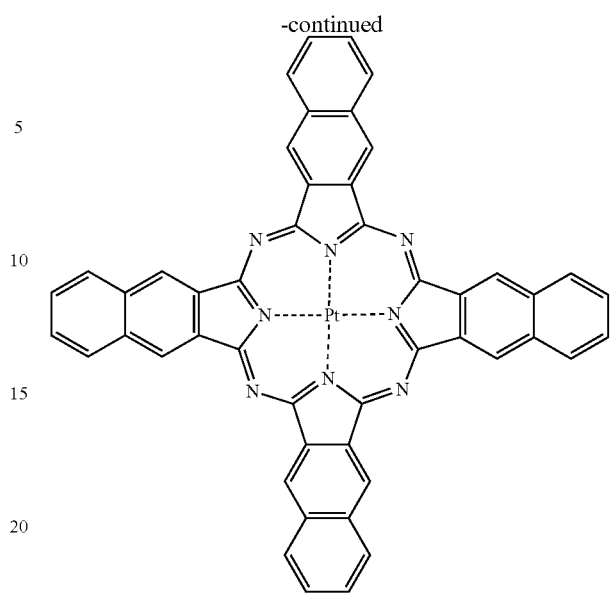

The content of the aforementioned phosphorescent dopant in the light-emitting layer is preferably in the range of 1 to 50 wt %, more preferably 5 to 30 wt %.

It is preferable to use an indolocarbazole compound represented by the aforementioned general formula (1) as a host material in the light-emitting layer. However, in the case where the said indolocarbazole compound is used in an organic layer other than the light-emitting layer, a host material other than the indolocarbazole compound may be used in the light-emitting layer. Further, the indolocarbazole compound may be used together with other host material. Still further, plural kinds of known host materials may be used together.

Among the known host compounds, the ones suitable for use preferably have a hole transport ability or an electron transport ability, can prevent the wavelength of emitted light from shifting to longer wavelengths, and have a high glass transition temperature.

Such known host materials are described in a large number of patent documents and elsewhere and a suitable material may be selected from them. Specific examples include, but are not limited to, indole derivatives, carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidene-based compounds, porphyrin-based compounds, anthraquinodimethan derivatives, anthrone derivatives, diphenylquinone derivatives, thiopyran dioxide derivatives, heterocyclic tetracarboxylic acid anhydrides of naphthalene and perylene, a variety of metal complexes represented by metal complexes of phthalocyanine derivatives and 8-quinolinol derivatives, metal phthalocyanines, and metal complexes of benzoxazole derivatives and benzothiazole derivatives, and polymer compounds such as polysilane-based compounds, poly(N-vinylcarbazole) derivatives, aniline-based copolymers, thiophene oligomers, polythiophene derivatives, polyphenylene derivatives, polyphenylenevinylene derivatives, and polyfluorene derivatives.

—Injecting Layer—

The injecting layer is a layer which is provided between an electrode and an organic layer to reduce the driving voltage and improve the luminance. The injecting layer includes a hole-injecting layer and an electron-injecting layer and may be provided respectively between the anode and the light-emitting layer or the hole-transporting layer and between the cathode and the light-emitting layer or the electron-transporting layer. The injecting layer may be provided according to the need.

—Hole-Blocking Layer—

The hole-blocking layer has a function of the electron-transporting layer in a broad sense and is composed of a hole-blocking material that has an extremely poor ability to transport holes while having a function of transporting electrons. The hole-blocking layer can improve the probability of recombination of electrons and holes by transporting electrons while blocking holes.

It is preferable to use an indolocarbazole compound represented by general formula (1) in the hole-blocking layer. However, in the case where the said indolocarbazole compound is used in an organic layer other than the hole-blocking layer, a known hole-blocking material may be used instead. Further, any one of the materials for the electron-transporting layer to be described later on may be used as a hole-blocking material according to the need.

—Electron-Blocking Layer—

The electron-blocking layer is made from a material that has an extremely poor ability to transport electrons while having a function of transporting holes and it can improve the probability of recombination of electrons and holes by transporting holes while blocking electrons.

As a material for the electron-blocking layer, any one of the materials for the hole-transporting layer to be described later on may be used according to the need. The thickness of the electron-blocking layer is preferably 3 to 100 nm, more preferably 5 to 30 nm.

—Exciton-Blocking Layer—

The exciton-blocking layer is a layer for blocking excitons that are generated by the recombination of holes and electrons in the light-emitting layer from diffusing to the charge-transporting layer. The insertion of this layer makes it possible to efficiently confine excitons in the light-emitting layer and enhance the luminous efficiency of the device. The exciton-blocking layer may be inserted either on the anode side or on the cathode side adjacent to the light-emitting layer or simultaneously on both the anode and the cathode sides.

Examples of a material for the exciton-blocking layer include 1,3-dicarbazolylbenzene (mCP) and bis(2-methyl-8-quinolinolato)-4-phenylphenolatoaluminum(III) (BAlq).

—Hole-Transporting Layer—

The hole-transporting layer is made from a hole-transporting material that has a function of transporting holes and it may be provided in a single layer or a plurality of layers.

The hole-transporting material has either a property of injecting or transporting holes or a property of constituting a barrier to electrons and it may be either an organic substance or an inorganic substance. Specific examples of known hole-transporting materials suitable for use include triazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, aniline-based copolymers, and electrically conductive oligomers, particularly thiophene oligomers. Preferable examples include porphyrin compounds, aromatic tertiary amine compounds, and styrylamine compounds and more preferable examples include aromatic tertiary amine compounds.

—Electron-Transporting Layer—

The electron-transporting layer is made from a material that has a function of transporting electrons and may be provided in a single layer or a plurality of layers.

An electron-transporting material (serving also as a hole-blocking material in some cases) may be an arbitrary material so long as it has a function of transporting electrons that are injected from the cathode to the light-emitting layer. It is preferable to use an indolocarbazole derivative represented by general formula (1) in the electron-transporting layer, but an arbitrary material may be selected from the known compounds and used. Examples of such known compounds include nitro-substituted fluorene derivatives, diphenylquinone derivatives, thiopyran dioxide derivatives, carbodiimide, fluorenylidenemethane derivatives, anthraquinodimethan derivatives, anthrone derivatives, and oxadiazole derivatives. Further, thiadiazole derivatives that are derived from the aforementioned oxadiazole derivatives by substituting a sulfur atom for the oxygen atom of the oxadiazole ring and quinoxaline derivatives that have a quinoxaline ring known as an electron-withdrawing group may be used as electron-transporting materials. Further, polymer materials that contain any of these materials in the polymer chain or polymer materials whose backbone is constituted of any of these materials may be used.

EXAMPLES

This invention is explained in more detail hereinafter with reference to the examples. However, this invention is not limited to the examples and can be reduced to practice in various modes unless such a practice exceeds the gist of this invention.

The indolocarbazole compounds to be used in this invention were synthesized by the routes shown below. The compound numbers correspond to the numbers assigned to the aforementioned chemical formulas.

Synthetic Example 1

Synthesis of Compound 3-1

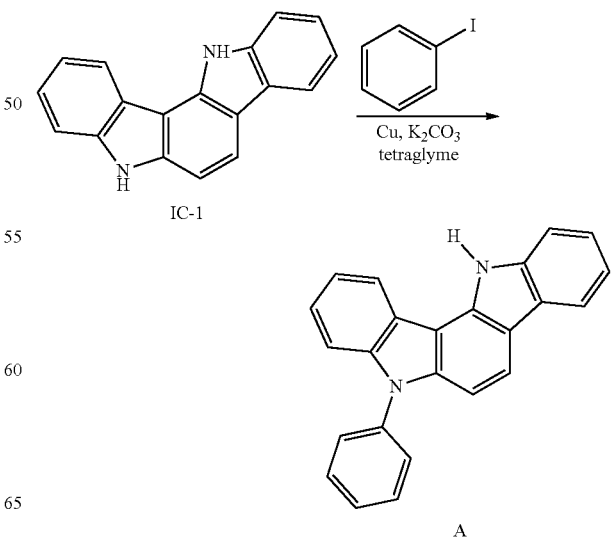

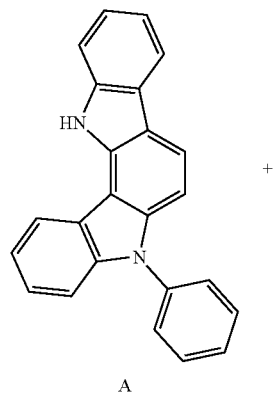

A

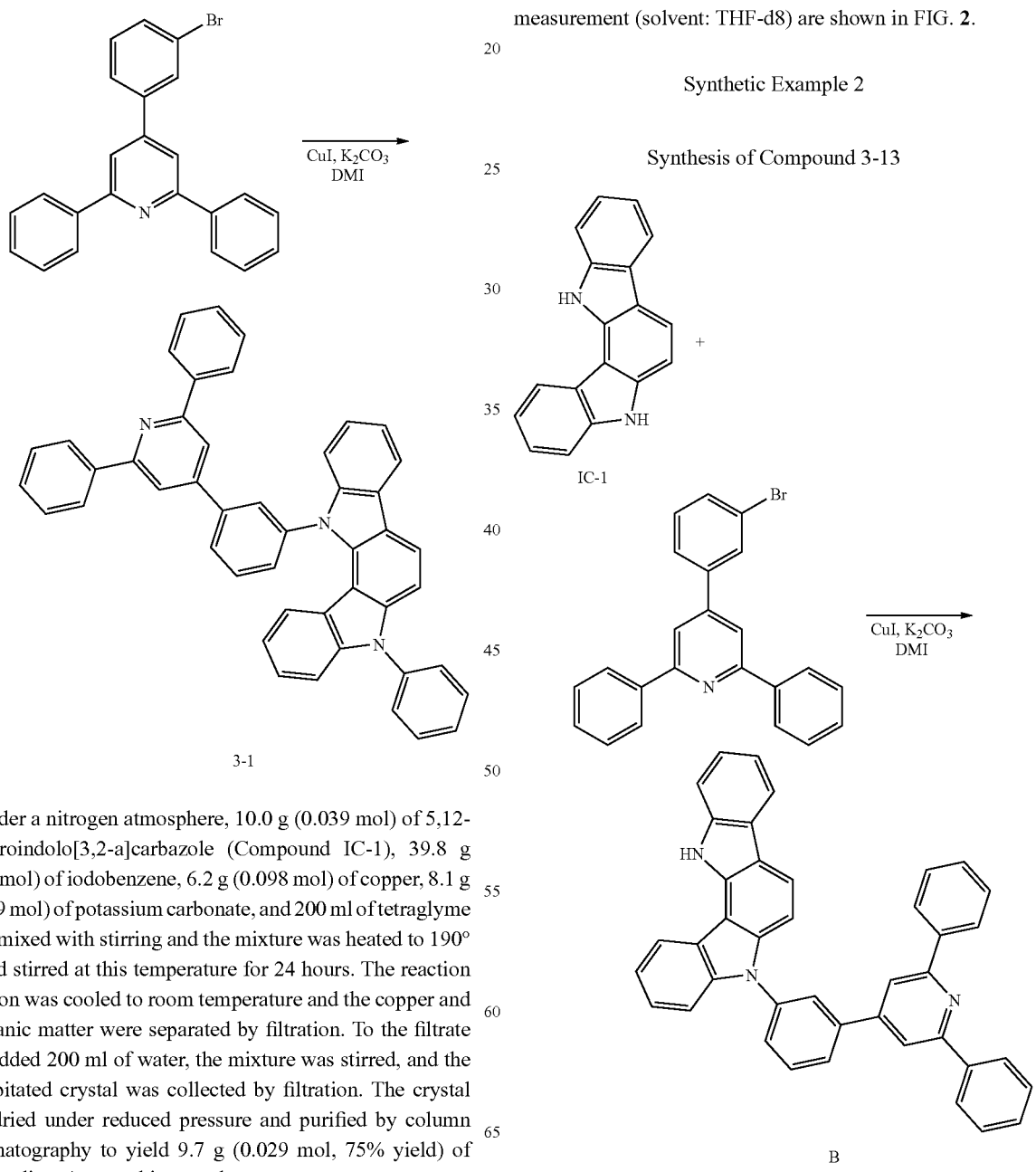

Under a nitrogen atmosphere, 10.0 g (0.039 mol) of 5,12-dihydroindolo[3,2-a]carbazole (Compound IC-1), 39.8 g (0.20 mol) of iodobenzene, 6.2 g (0.098 mol) of copper, 8.1 g (0.059 mol) of potassium carbonate, and 200 ml of tetraglyme were mixed with stirring and the mixture was heated to 190° C. and stirred at this temperature for 24 hours. The reaction solution was cooled to room temperature and the copper and inorganic matter were separated by filtration. To the filtrate was added 200 ml of water, the mixture was stirred, and the precipitated crystal was collected by filtration. The crystal was dried under reduced pressure and purified by column chromatography to yield 9.7 g (0.029 mol, 75% yield) of Intermediate A as a white powder.

Under a nitrogen atmosphere, 25.0 g (0.075 mol) of Intermediate A, 25.6 g (0.066 mol) of 4-(3-bromophenyl)-2,6-diphenylpyridine, 25.5 g (0.13 mol) of copper iodide, 31.0 g (0.22 mol) of potassium carbonate, and 500 ml of 1,3-dimethyl-2-imidazolidinone were mixed and the mixture was heated at 185° C. for 45 hours with stirring. The reaction solution was cooled to room temperature and inorganic matter was separated by filtration. The filtrate was added to 4,000 ml of water, the mixture was stirred, and the precipitated crystal was collected by filtration. The crystal was dried under reduced pressure and purified by column chromatography to yield 23.7 g (0.037 mol, 56% yield) of Compound 3-1 as a white powder.

Figure 2:
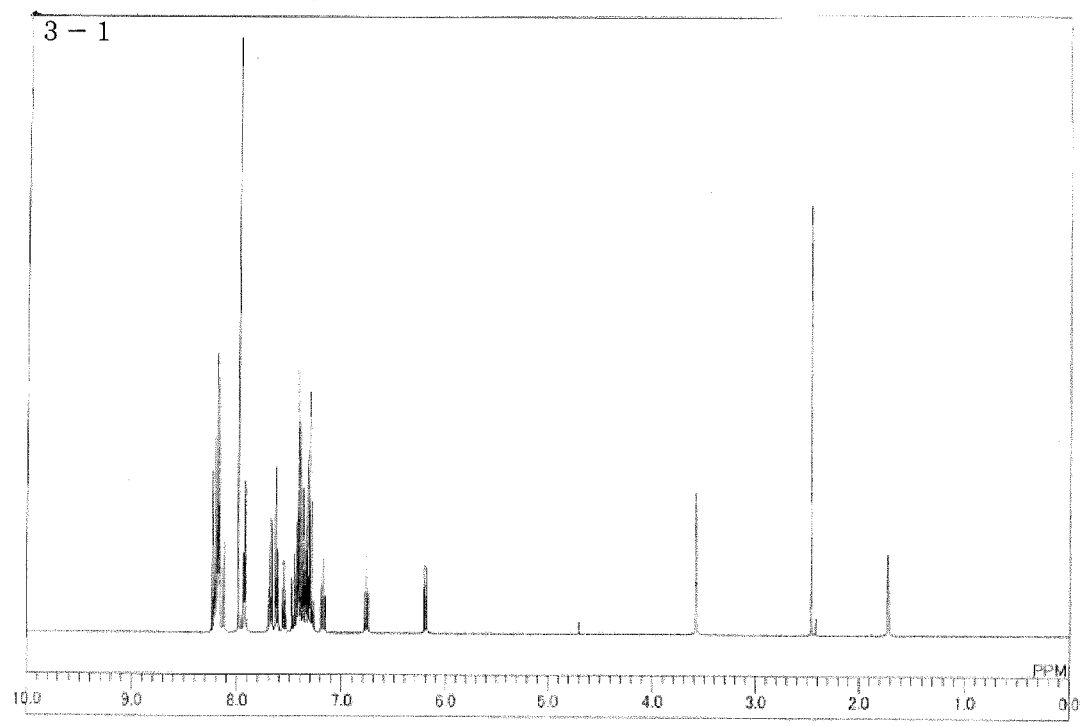
FIG. 2 shows a $^1$H-NMR chart of Compound 3-1.

APCI-TOFMS: m/z 638 [M+H]$^+$. The results of $^1$H-NMR measurement (solvent: THF-d8) are shown in FIG. 2.

Synthetic Example 2

Synthesis of Compound 3-13

-continued

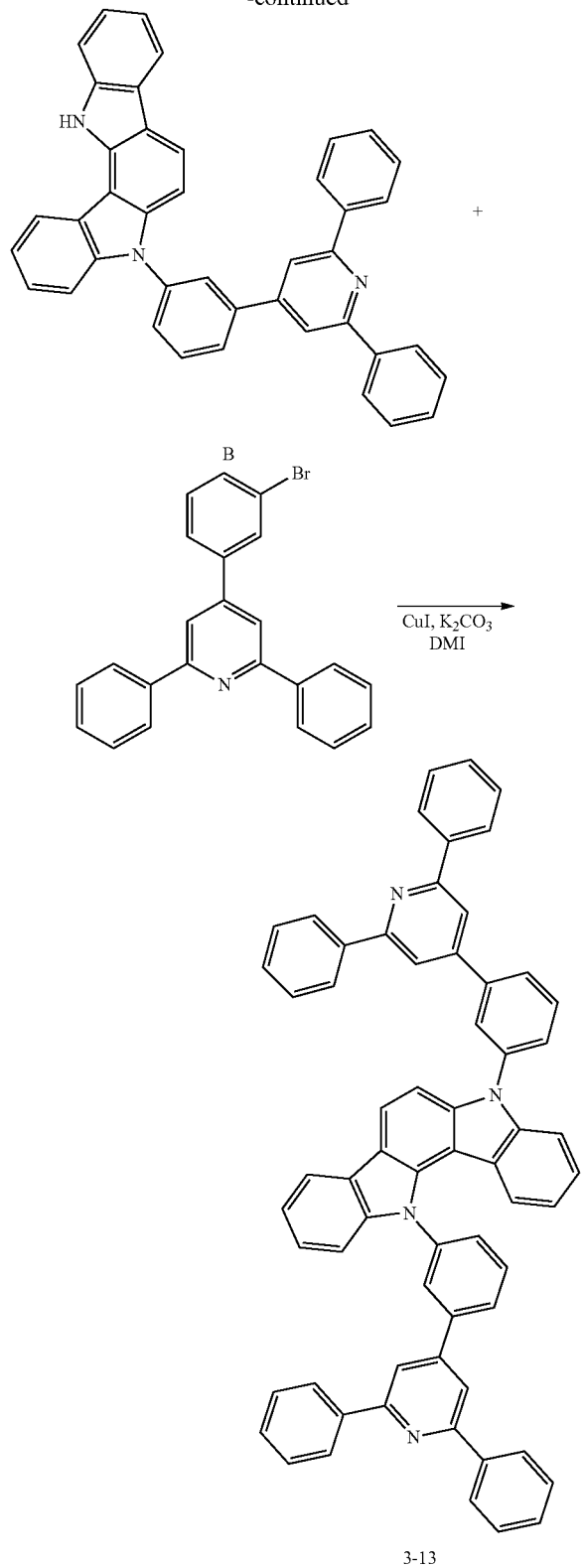

3-13

Under a nitrogen atmosphere, 9.9 g (0.039 mol) of Compound IC-1, 14.6 g (0.038 mol) of 4-(3-bromophenyl)-2,6-diphenylpyridine, 13.5 g (0.071 mol) of copper iodide, 16.6 g (0.12 mol) of potassium carbonate, and 350 ml of 1,3-dimethyl-2-imidazolidinone were mixed and the mixture was heated at 185° C. for 30 hours with stirring. The reaction solution was cooled to room temperature and inorganic matter was separated by filtration. The filtrate was added to 4,000 ml of water, the mixture was stirred, and the precipitated crystal was collected by filtration. The crystal was dried under reduced pressure and purified by column chromatography to yield 20.5 g (0.036 mol, 94% yield) of Intermediate B as a white powder.

Under a nitrogen atmosphere, 19.1 g (0.034 mol) of Intermediate B, 12.9 g (0.034 mol) of 4-(3-bromophenyl)-2,6-diphenylpyridine, 12.2 g (0.064 mol) of copper iodide, 15.8 g (0.12 mol) of potassium carbonate, and 300 ml of 1,3-dimethyl-2-imidazolidinone were mixed and the mixture was heated at 185° C. for 45 hours with stirring. The reaction solution was cooled to room temperature and inorganic matter was separated by filtration. The filtrate was added to 4,000 ml of water, the mixture was stirred, and the precipitated crystal was collected by filtration. The crystal was dried under reduced pressure and purified by column chromatography to yield 8.3 g (0.010 mol, 28% yield) of Compound 343 as a white powder.

Figure 3:
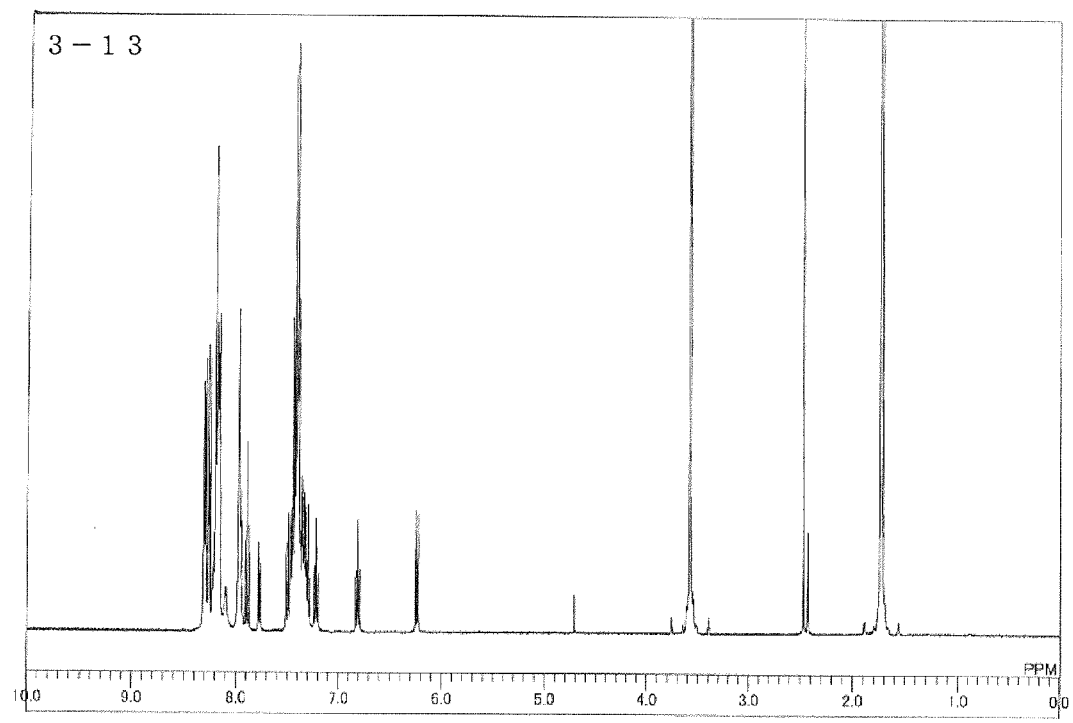
FIG. 3 shows a $^1$H-NMR chart of Compound 3-13.

APCI-TOFMS: m/z 867 [M+H]$^+$. The results of $^1$H-NMR measurement (solvent: THF-d8) are shown in FIG. 3.

Compounds 1-11, 1-15, 2-6, 2-30, 3-3, 3-23, and 4-3 were prepared according to the methods described in the aforementioned Synthetic Examples and in the specification and used in the fabrication of organic EL devices.

Example 1

The constituent layers were deposited in thin film by the vacuum deposition process at a degree of vacuum of $4.0 \times 10^{-5}$ Pa one upon another on a glass substrate on which a 110 nm-thick indium tin oxide (ITO) anode had been formed. First, copper phthalocyanine (CuPC) was deposited on the ITO anode to a thickness of 25 nm. Then, 4,4'-bis[N-(1-naphthyl)-N-phenylamino]biphenyl (NPB) was deposited to a thickness of 40 nm as a hole-transporting layer. Next, Compound 3-1 obtained in Synthetic Example as a host material and tris(2-phenylpyridine)iridium(III) (Ir(ppy)$_3$) as a phosphorescent dopant were co-deposited on the hole-transporting layer from different deposition sources to a thickness of 40 nm as a light-emitting layer. The concentration of Ir(ppy)$_3$ in the light-emitting layer was 10.0 wt %. Next, tris(8-hydroxyquinolinato)aluminum (III) (Alq3) was deposited to a thickness of 20 nm as an electron-transporting layer. Further, lithium fluoride (LiF) was deposited on the electron-transporting layer to a thickness of 1.0 nm as an electron-injecting layer. Finally, aluminum (Al) as an electrode was deposited on the electron-injecting layer to a thickness of 70 nm to finish the fabrication of an organic EL device.

Example 2

An organic EL device was fabricated as in Example 1 except that Compound 1-11 was used as the host material in the light-emitting layer.

Example 3

An organic EL device was fabricated as in Example 1 except that Compound 1-15 was used as the host material in the light-emitting layer.

Example 4

An organic EL device was fabricated as in Example 1 except that Compound 2-6 was used as the host material in the light-emitting layer.

Example 5

An organic EL device was fabricated as in Example 1 except that Compound 2-30 was used as the host material in the light-emitting layer.

Example 6

An organic EL device was fabricated as in Example 1 except that Compound 3-3 was used as the host material in the light-emitting layer.

Example 7

An organic EL device was fabricated as in Example 1 except that Compound 3-13 was used as the host material in the light-emitting layer.

Example 8

An organic EL device was fabricated as in Example 1 except that Compound 3-23 was used as the host material in the light-emitting layer.

Example 9

An organic EL device was fabricated as in Example 1 except that Compound 4-3 was used as the host material in the light-emitting layer.

Comparative Example 1

An organic EL device was fabricated as in Example 1 except that 4,4'-bis(9-carbazolyl)biphenyl (CBP) was used as the host material in the light-emitting layer.

Comparative Example 2

An organic EL device was fabricated as in Example 1 except that Compound H-1 shown below was used as the host material in the light-emitting layer.

Comparative Example 3

An organic EL device was fabricated as in Example 1 except that Compound H-2 shown below was used as the host material in the light-emitting layer.

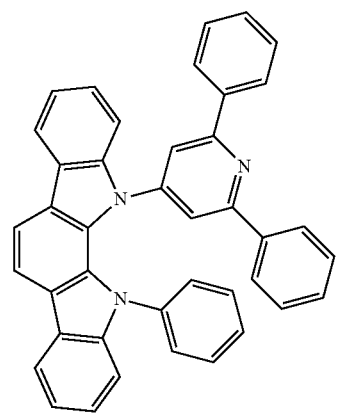

H-1

-continued

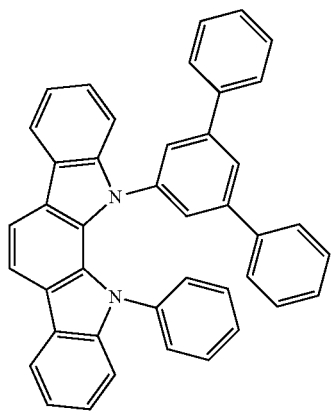

H-2

Each of the organic EL devices fabricated in Examples 1 to 9 and Comparative Examples 1 to 3 was connected to an external power source and, when direct current voltage was applied, the device was confirmed to have the luminous characteristics shown in Table 1. In Table 1, the values of the luminance, voltage, and luminous efficiency are obtained when the device was driven at 10 mA/cm$^2$. The peak wavelength of the spectrum of light emitted from the device is 530 nm and it was identified that light is emitted from Ir(ppy)$_3$.

TABLE 1

|   | Compound | Luminance (cd/m$^2$) | Voltage (V) | Luminous efficiency (lm/W) |
|---|---|---|---|---|
| Example 1 | 3-1 | 3030 | 6.9 | 13.8 |
| 2 | 1-11 | 2730 | 6.9 | 12.4 |
| 3 | 1-15 | 2950 | 6.6 | 14.0 |
| 4 | 2-6 | 2990 | 6.5 | 14.5 |
| 5 | 2-30 | 2870 | 6.9 | 13.1 |
| 6 | 3-3 | 2790 | 6.2 | 14.1 |
| 7 | 3-13 | 3240 | 7.0 | 14.5 |
| 8 | 3-23 | 2950 | 7.0 | 13.2 |
| 9 | 4-3 | 2860 | 6.1 | 14.7 |
| Comparative Example 1 | CBP | 2420 | 9.3 | 8.2 |
| 2 | H-1 | 2840 | 7.4 | 12.1 |
| 3 | H-2 | 535 | 8.2 | 2.0 |

It is apparent from Table 1 that the indolocarbazole compounds to be used in the organic EL devices of this invention display good luminous characteristics in comparison with CBP, a compound generally known as a phosphorescent host. Moreover, they display better luminous characteristics than Compound H-1 in which an aromatic heterocyclic ring is directly linked to indolocarbazole or Compound H-2 in which no aromatic heterocyclic ring is linked to indolocarbazole and this proves the superior performance of the aforementioned indolocarbazole compounds.

Example 10

The constituent layers were deposited in thin film by the vacuum deposition process at a degree of vacuum of 2.0×10$^{-5}$ Pa one upon another on a glass substrate on which a 110 nm-thick indium tin oxide (ITO) anode had been formed. First, copper phthalocyanine (CuPC) was deposited on the ITO anode to a thickness of 25 nm as a hole-injecting layer. Then, NPB was deposited to a thickness of 90 nm as a hole-transporting layer. Next, Compound 3-1 as a host material and iridium(III)bis[(4,6-difluorophenyl)-pyridinato-N,C2']picolinate (FIrpic), a phosphorescent blue light-emitting iridium complex, as a dopant were co-deposited on the hole-transporting layer from different deposition sources to a thickness of 30 nm as a light-emitting layer. The concentration of FIrpic was 10 wt %. Next, Alq3 was deposited to a thickness of 30 nm as an electron-transporting layer. Further, LiF was deposited on the electron-transporting layer to a thickness of 1.0 nm as an electron-injecting layer. Finally, Al as an electrode was deposited on the electron-injecting layer to a thickness of 70 nm. The organic EL device thus fabricated has a layered structure formed by inserting an electron-injecting layer between the cathode and the electron-transporting layer in the device illustrated in FIG. 1.

Example 11

An organic EL device was fabricated as in Example 10 except that Compound 3-4 was used as the host material in the light-emitting layer.

Example 12

An organic EL device was fabricated as in Example 10 except that Compound 3-23 was used as the host material in the light-emitting layer.

Comparative Example 4

An organic EL device was fabricated as in Example 10 except that CBP was used as the host material in the light-emitting layer.

Comparative Example 5

An organic EL device was fabricated as in Example 10 except that Compound H-1 was used as the host material in the light-emitting layer.

Each of the organic EL devices fabricated in Examples 10 to 12 and Comparative Examples 4 and 5 was connected to an external power source and, when direct current voltage was applied, the device was confirmed to have the luminous characteristics shown in Table 2. In Table 2, the values of the luminance, voltage, and luminous efficiency are obtained when the device was driven at 2.5 mA/cm$^2$. The peak wavelength of the spectrum of light emitted from the device is 475 nm and it was identified that light is emitted from FIrpic.

TABLE 2

|  | Compound | Luminance (cd/m$^2$) | Voltage (V) | Luminous efficiency (lm/W) |
| --- | --- | --- | --- | --- |
| Example 10 | 3-1 | 130 | 7.5 | 2.2 |
| Example 11 | 3-4 | 135 | 7.9 | 2.1 |
| Example 12 | 3-23 | 125 | 7.4 | 2.1 |
| Comp. Ex. 4 | CBP | 90 | 8.5 | 1.3 |
| Comp. Ex. 5 | H-1 | 55 | 8.1 | 0.9 |

It is also apparent from Table 2 that the organic EL devices in the Examples display better luminous characteristics that those in the Comparative Examples and this proves the superiority of this invention.

INDUSTRIAL APPLICABILITY

The organic EL device of this invention satisfies a level of performance required for practical use with respect to the luminous characteristics, driving life, and durability and is of high technical value because of its potential applicability to flat panel displays (cellular phone display devices, vehicle-mounted display devices, office computer display devices, and television sets), light sources utilizing the characteristics of planar light emitters (illumination, light sources for copying machines, and backlight sources for liquid crystal displays and meters), display boards, and marker lamps.

The invention claimed is:

1. An organic electroluminescent device comprising an anode, organic layers containing a phosphorescent light-emitting layer, and a cathode piled one upon another on a substrate wherein an organic layer is a light-emitting layer and contains an indolocarbazole compound represented by general formula (1);

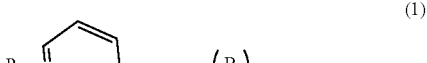

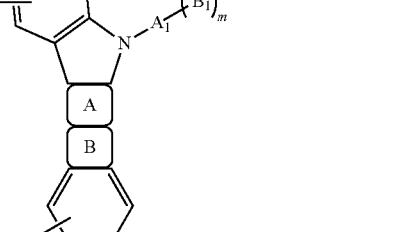

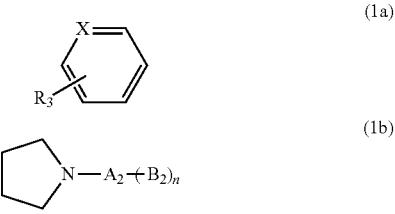

in general formula (1), ring A is an aromatic ring or a heterocyclic ring represented by formula (1a) and fused to the adjacent rings at arbitrary positions and ring B is a heterocyclic ring represented by formula (1b) and fused to the adjacent rings at arbitrary positions; in general formula (1) and formulas (1a) and (1b), each of $A_1$ and $A_2$ is independently an (m+1)-valent or (n+1)-valent aromatic hydrocarbon group of 6 to 50 carbon atoms and has no substituent or has one to six substituents selected from an alkyl group of 1 to 4 carbon atoms, an alkoxyl group of 1 to 2 carbon atoms, and an acetyl group, provided that when a number of the substituents is 2 or more, they may be identical with or different from one another;

each of $B_1$ and $B_2$ is independently:

(i) an aromatic heterocyclic group of 3 to 17 carbon atoms, or (ii) an aromatic heterocyclic group of 6 to 50 carbon atoms in total in which two to five aromatic heterocyclic rings, each of which have a total of 3 to 17 carbon atoms, are linked together such that any two linked aromatic heterocyclic rings are connected via a single bond, and each of $B_1$ and $B_2$ has no substituent or has one to six substituents selected from an alkoxyl group of 1 to 2 carbon atoms, an acetyl group, and an aromatic hydrocarbon group of 6 to 12 carbon atoms, provided that when a number of the substituents is 2 or more, they may be identical with or different from one another; X is a methine group; each of $R_1$ and $R_2$ is independently a hydrogen atom, an aliphatic hydrocarbon group of 1 to 10 carbon atoms, an aromatic hydrocarbon group of 6 to 12 carbon atoms, or an aromatic heterocyclic group of 3 to 11 carbon atoms; $R_3$ is a hydrogen atom, an aliphatic hydrocarbon group of 1 to 10 carbon atoms, an aromatic hydrocarbon group of 6 to 12 carbon atoms, or an aromatic heterocyclic group of 3 to 11 carbon atoms; m is an integer of 1 to 3; n is an integer of 0 to 3; when m or n is 2 or more, a plurality of $B_1$s or $B_2$s may be identical with or different from one another.

2. An organic, electroluminescent device as described in claim 1 wherein the indolocarbazole compound represented by general formula (1) is an indolocarbazole compound represented by any one of general formulas (2) to (5);

3. An organic electroluminescent device as described in claim 2 wherein the indolocarbazole compound represented by any one of general formulas (2) to (5) is an indolocarbazole compound represented by any one of general formulas (6) to (9);

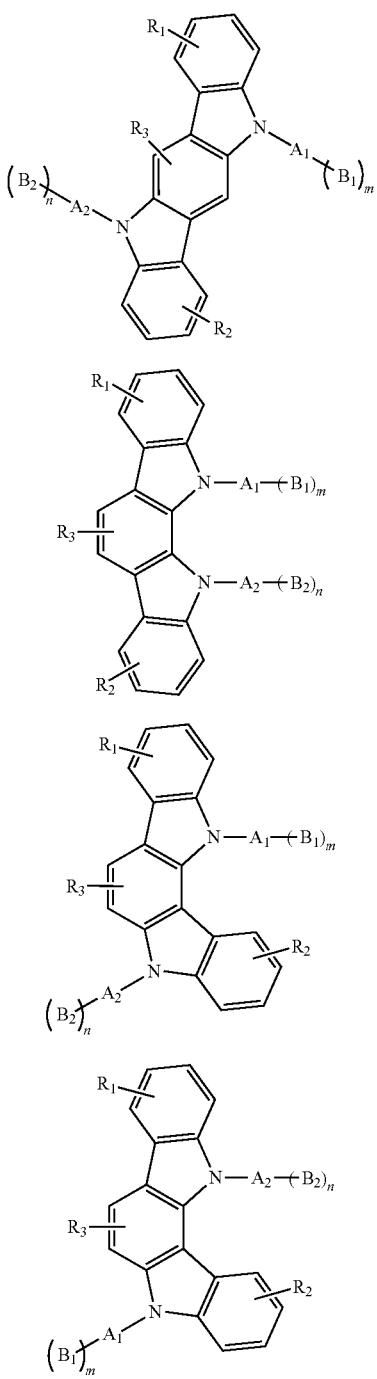

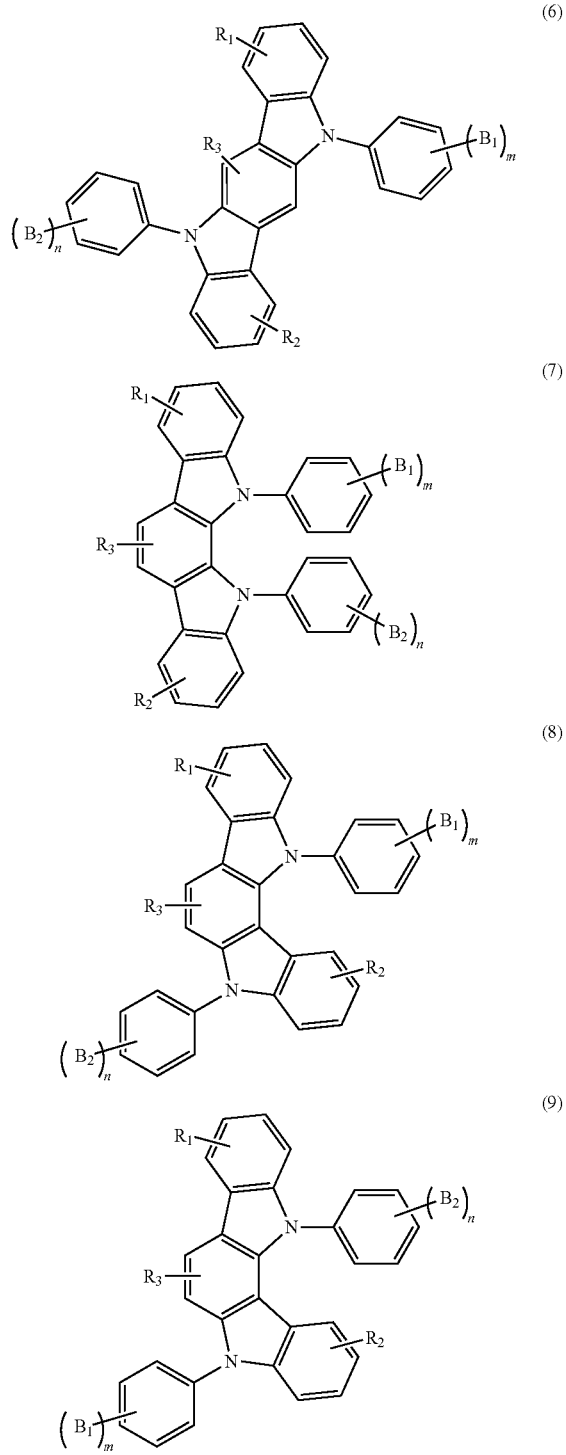

In general formulas (2) to (5), $A_1$, $A_2$, $B_1$, $B_2$, $R_1$ to $R_3$, m, and n respectively have the same meaning as those in general formula (1).

In general formulas (6) to (9), $B_1$, $B_2$, $R_1$ to $R_3$, m, and n respectively have the same meaning as those in general formula (1).

4. An organic electroluminescent device as described in claim 1 wherein the organic layer containing an indolocarbazole compound is a light-emitting layer containing a phosphorescent dopant.

5. An organic electroluminescent device as described in claim 2 wherein the organic layer containing an indolocarbazole compound is a light-emitting layer containing a phosphorescent dopant having a peak emission wavelength of 440 to 510 nm and an indolocarbazole compound represented by general formula (4) or (5).

6. An organic electroluminescent device as described in claim 2 wherein the organic layer containing an indolocarbazole compound is a light-emitting layer containing a phosphorescent dopant.

7. An organic electroluminescent device as described in claim 3 wherein the organic layer containing an indolocarbazole compound is a light-emitting layer containing a phosphorescent dopant.

8. An organic electroluminescent device as described in claim 1 wherein each of $B_1$ and $B_2$ is independently an aromatic heterocyclic group derived from pyrrole, pyridine, pyrimidine, triazine, indole, quinoline, isoquinoline, quinoxaline, naphthyridine, carbazole, acridine, furan, benzofuran, dibenzofuran, thiopene, benzothiophene, dibenzothiophene, bipyridine, bipyrimidine, bitriazine, pyridylpyrimidine, pyridylcarbazole, pyridylpyrimidine, pyridylcarbazole, or pyrimidylcarbazole, and may have one to six substituents selected from an alkoxyl group of 1 to 2 carbon atoms, an acetyl group, and an aromatic hydrocarbon group of 6 to 12 carbon atoms, provided that when a number of the substituents is 2 or more, they may be identical with or different from one another.

9. An organic electroluminescent device as described in claim 1 wherein each of $A_1$ and $A_2$ is independently an aromatic hydrocarbon group derived from benzene, naphthalene, fluorene, anthracene, phenanthrene, fluoranthene, pyrene, chrysene, biphenyl, terphenyl, phenylnaphthalene, diphenylnaphthalene, phenylanthracene, diphenylanthracene, or diphenylfluorene, and may have one to six substituents selected from an alkyl group of 1 to 4 carbon atoms, an alkoxyl group of 1 to 2 carbon atoms, and an acetyl group, provided that when a number of the substituents is 2 or more, they may be identical with or different from one another.

10. An organic electroluminescent device comprising an anode, organic layers containing a phosphorescent light-emitting layer, and a cathode piled one upon another on a substrate wherein an organic layer is a light-emitting layer and contains an indolocarbazole compound represented by general formula (1);

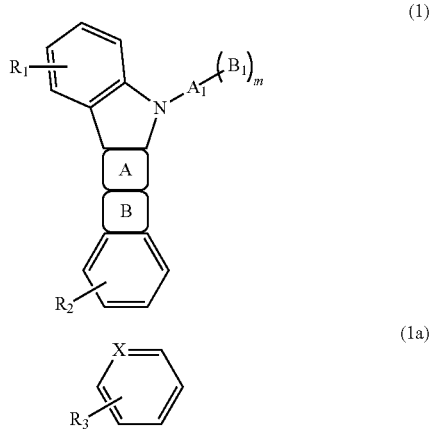

(1)

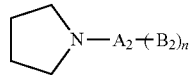

(1b)

in general formula (1), ring A is an aromatic ring or a heterocyclic ring represented by formula (1a) and fused to the adjacent rings at arbitrary positions and ring B is a heterocyclic ring represented by formula (1b) and fused to the adjacent rings at arbitrary positions; in general formula (1) and formulas (1a) and (1b), each of $A_1$ and $A_2$ is independently an (m+1)-valent or (n+1)-valent aromatic hydrocarbon group of 6 to 50 carbon atoms and has no substituent or has one to six substituents selected from an alkyl group of 1 to 4 carbon atoms, an alkoxyl group of 1 to 2 carbon atoms, and an acetyl group, provided that when a number of the substituents is 2 or more, they may be identical with or different from one another;

each of $B_1$ and $B_2$ is independently:

(i) an aromatic heterocyclic group of 3 to 17 carbon atoms, or (ii) an aromatic heterocyclic group of 6 to 50 carbon atoms in total in which two to five aromatic heterocyclic rings, each of which have a total of 3 to 17 carbon atoms, are linked together such that any two linked aromatic heterocyclic rings are connected via a single bond, and each of $B_1$ and $B_2$ has no substituent or has one to six substituents, each of said substituents being an aromatic hydrocarbon group of 6 to 12 carbon atoms, provided that when a number of the substituents is 2 or more, they may be identical with or different from one another; X is a methine group; each of $R_1$ and $R_2$ is independently a hydrogen atom, an aliphatic hydrocarbon group of 1 to 10 carbon atoms, an aromatic hydrocarbon group of 6 to 12 carbon atoms, or an aromatic heterocyclic group of 3 to 11 carbon atoms; $R_3$ is a hydrogen atom, an aliphatic hydrocarbon group of 1 to 10 carbon atoms, an aromatic hydrocarbon group of 6 to 12 carbon atoms, or an aromatic heterocyclic group of 3 to 11 carbon atoms; m is an integer of 1 to 3; n is an integer of 0 to 3; when m or n is 2 or more, a plurality of $B_1$s or $B_2$s may be identical with or different from one another.

11. An organic electroluminescent device as described in claim 10 wherein the indolocarbazole compound represented by general formula (1) is an indolocarbazole compound represented by any one of general formulas (2) to (5);

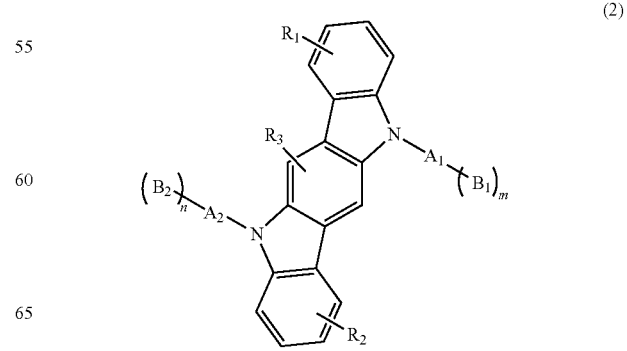

(2)

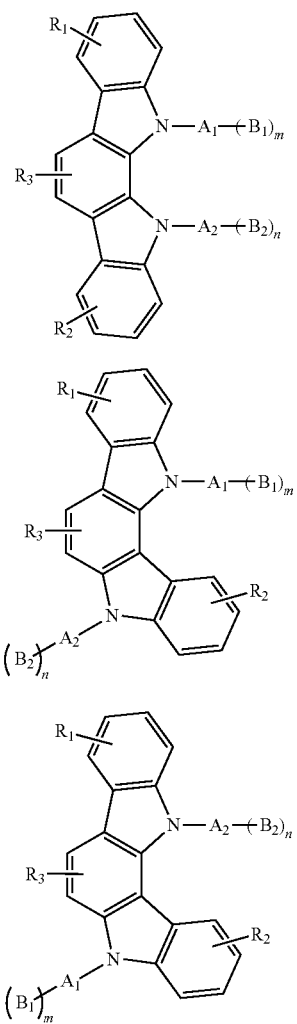

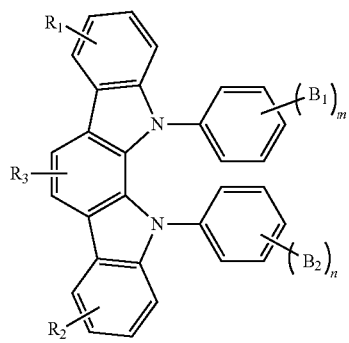

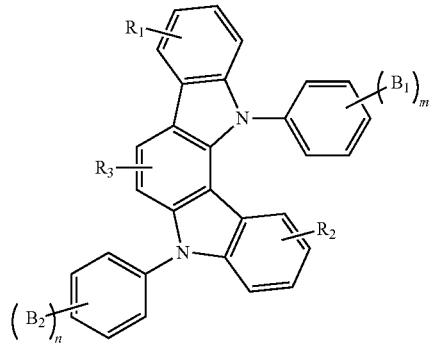

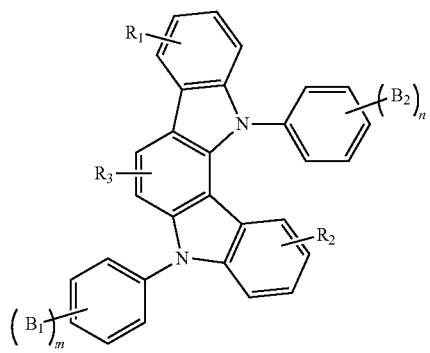

in general formulas (2) to (5), $A_1$, $A_2$, $B_1$, $B_2$, $R_1$ to $R_3$, m, and n respectively have the same meaning as those in general formula (1).

12. An organic electroluminescent device as described in claim 11 wherein the indolocarbazole compound represented by any one of general formulas (2) to (5) is an indolocarbazole compound represented by any one of general formulas (6) to (9);

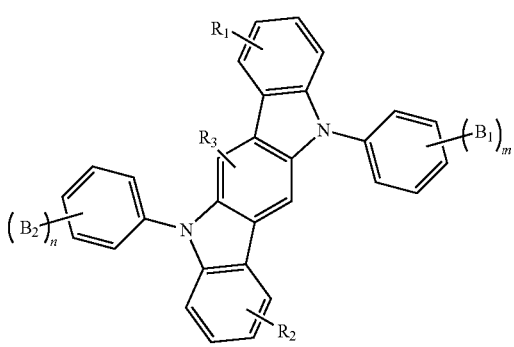

In general formulas (6) to (9), $B_1$, $B_2$, $R_1$ to $R_3$, m, and n respectively have the same meaning as those in general formula (1).

13. An organic electroluminescent device as described in claim 10 wherein the organic layer containing an indolocarbazole compound is a light-emitting layer containing a phosphorescent dopant.

14. An organic electroluminescent device as described in claim 11 wherein the organic layer containing an indolocarbazole compound is a light-emitting layer containing a phosphorescent dopant having a peak emission wavelength of 440 to 510 nm and an indolocarbazole compound represented by general formula (4) or (5).

15. An organic electroluminescent device as described in claim 11 wherein the organic layer containing an indolocarbazole compound is a light-emitting layer containing a phosphorescent dopant.

16. An organic electroluminescent device as described in claim 12 wherein the organic layer containing an indolocarbazole compound is a light-emitting layer containing a phosphorescent dopant.

17. An organic electroluminescent device as described in claim 10 wherein each of $B_1$ and $B_2$ is independently an aromatic heterocyclic group derived from pyrrole, pyridine, pyrimidine, triazine, indole, quinoline, isoquinoline, quinoxaline, naphthyridine, carbazole, acridine, furan, benzofuran, dibenzofuran, thiopene, benzothiophene, dibenzothiophene, bipyridine, bipyrimidine, bitriazine, pyridylpyrimidine, pyridylcarbazole, pyridylpyrimidine, pyridylcarbazole, or pyrimidylcarbazole, and may have one to six substituents, each of said substituents being an aromatic hydrocarbon group of 6 to 12 carbon atoms, provided that when a number of the substituents is 2 or more, they may be identical with or different from one another.

18. An organic electroluminescent device as described in claim 10 wherein each of $A_1$ and $A_2$ is independently an aromatic hydrocarbon group derived from benzene, naphthalene, fluorene, anthracene, phenanthrene, fluoranthene, pyrene, chrysene, biphenyl, terphenyl, phenylnaphthalene, diphenylnaphthalene, phenylanthracene, diphenylanthracene, or diphenylfluorene, and may have one to six substituents selected from an alkyl group of 1 to 4 carbon atoms, an alkoxyl group of 1 to 2 carbon atoms, and an acetyl group, provided that when a number of the substituents is 2 or more, they may be identical with or different from one another.

* * * * *